United States Patent [19]

Johnson et al.

[11] Patent Number: 4,873,360

[45] Date of Patent: Oct. 10, 1989

[54] PROCESS FOR THE PREPARATION OF CYCLOPENTANOIDS AND NOVEL INTERMEDIATES PRODUCED THEREBY

[75] Inventors: Carl R. Johnson; Thomas D. Penning, both of Detroit, Mich.

[73] Assignee: Board of Governors of Wayne State University, Detroit, Mich.

[21] Appl. No.: 146,716

[22] Filed: Jan. 21, 1988

Related U.S. Application Data

[62] Division of Ser. No. 883,993, Jul. 10, 1986, abandoned.

[51] Int. Cl.$^4$ ............................................. C07C 177/00
[52] U.S. Cl. .................................... 560/121; 549/436; 549/437; 562/503
[58] Field of Search ......................... 560/121; 562/503

[56] References Cited

PUBLICATIONS

Crabbe et al., J. Chem. Soc. Chem Comm, 1972, 1126.
Kirk Othmer Supplement, pp. 711–752, (1984).
Noyori, R., et al., Angew. Chem., Int. Ed., Engl., 23, 847, (1984).
McDonald, C. E.; Dugger, R. W., "Abstract of Papers", 186th Nat'l. Meeting of the Am. Chemical Soc., Washington, D.C., Sep. 1983 ORGN 129 (1983).
Posternak, Th. in Helvetica Chemica Acta, 55, 2839–2844, (1972).
Cocu, F. G., et al., Helv. Chim. Acta., 55, 2828, 2838, (1972).
Kaneko, C., et al., Synthesis, 876, (1974).
Miura, S., et al., Tetrahedron, 32, 1893, (1976).
Laumen, K., et al., Tetrahedron Lett., 5875, (1984).
Deardorff, D. R., et al., Tetrahedron Lett., 1255, (1986).
VanRheenen, V., et. al., Tetrahedran Lett., 1973, (1976).
Kunnen, K. B., Dissertation, W.S.U., Detroit, Mich., (1985), (Abstract attached).
Pfitzner, K. E., et al., J. Am. Chem. Soc., 87, 5661, 5670, (1965).
Roos, G. I., et al., J. Am. Chem. Soc., 75, 422, (1953).
Bowden, K., et al., J. Chem. Soc., 39, (1946).
Johnson, C. R., et al., J. Am. Chem. Soc., 104, 4021, (1982).

Lim, M. I., et al., Tetrahedron Lett., 5559, (1983).
Dugger, R. W., Miami University, Ohio, personal communication, 1981$_4$, (telephone communication).
Suzuki, M., et al., Tetrahedron Lett., 5563, (1982).
Suzuki, M., et al., ibid. 1384, (1984).
Sih, C. J., et al., J. Am. Chem. Soc., 97, 865, (1975).
Suzuki, M., et al., J. Am. Chem. Soc., 107, 3348, (1985).
Corey, E., et al., J. Am. Chem. Soc., 95, 8483, (1973).
Dobson, N., et al., Tetrahedron, 16, 16, (1961).
Donaldson, R., et al., J. Am. Chem. Soc., 103, 2108, (1981)–See Footnote.

*Primary Examiner*—Robert Gerstl
*Attorney, Agent, or Firm*—Ian C. McLeod

[57] ABSTRACT

Cyclopentanoids (I) of the formula:

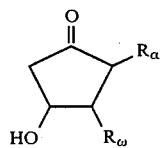

(I)

including stereoisomers are described along with a process for the preparation of I. In particular the preparation of prostanoids of the formula:

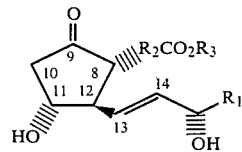

wherein $R_1$ is a alkyl group containing 1 to 8 carbon atoms and $R_2CO_2R_3$ is an alkenyl ester group, $R_2$ contains 2 to 6 carbon atoms and $R_3$ is a lower alkyl group containing 1 to 6 carbon atoms is described. A particular prostaglandin prepared by the process is PGE$_2$. The prostanoids have been demonstrated to have pharmacological activity in animals and humans. Novel intermediates of (I) are also described.

10 Claims, 1 Drawing Sheet

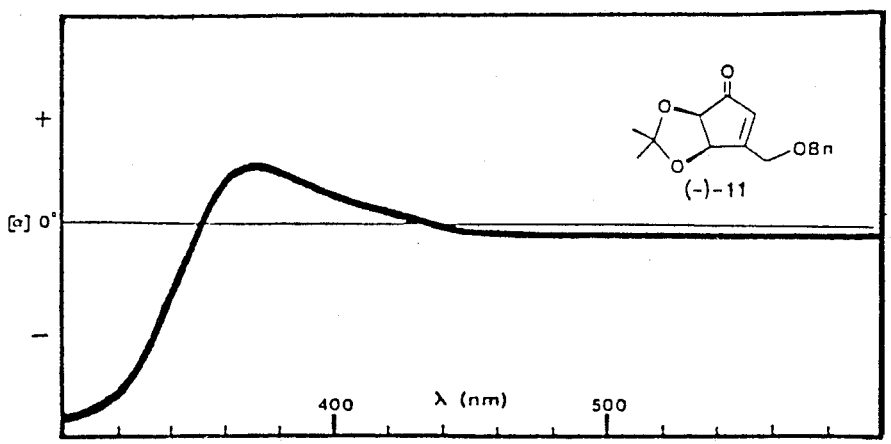
FIG. 1   ORD Curve of (−)-11.
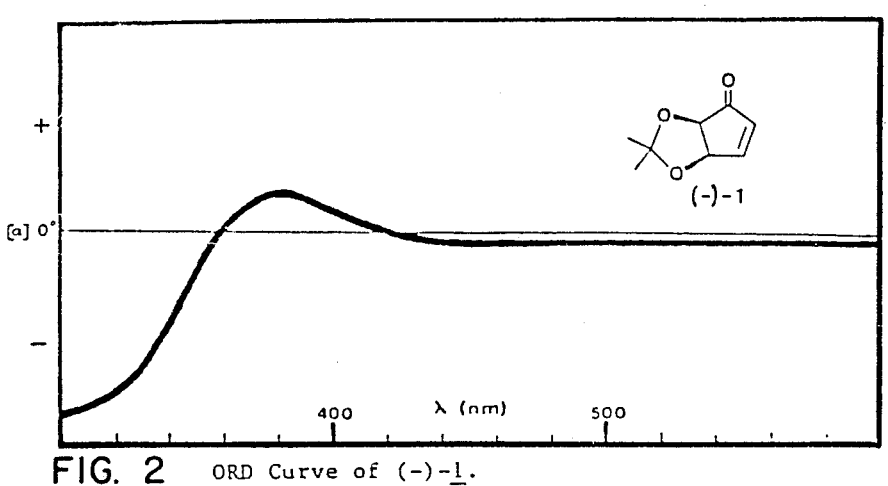
FIG. 2   ORD Curve of (−)-1.
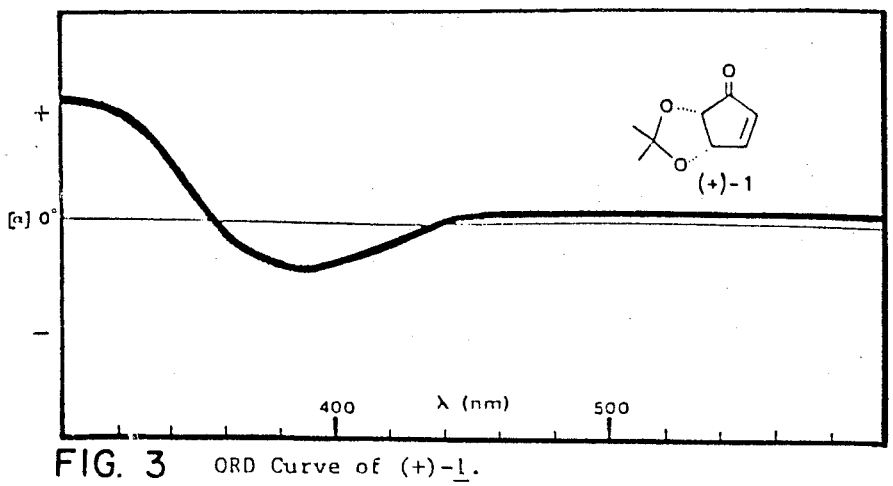
FIG. 3   ORD Curve of (+)-1.

PROCESS FOR THE PREPARATION OF CYCLOPENTANOIDS AND NOVEL INTERMEDIATES PRODUCED THEREBY

This is a divisional of co-pending application Ser. No. 883,993 filed on July 10, 1986, abandoned.

BACKGROUND OF THE INVENTION

(1) Field of the Invention

The present invention relates to a process for the preparation of cyclopentanoids particularly prostaglandins of the $PGE_2$ class. In particular the present invention relates to a process which utilizes a novel triply convergent synthetic technique to produce prostanoid stereoisomers in pure form using three separately prepared intermediates.

(2) Prior Art

The prostaglandins are described in detail in an excellent review found in *Kirk Othmer* Supplement 711–752 (1984). This reference also describes some known processes for the synthesis of these compounds, particularly the Corey process. This synthesis, which is lengthy and expensive, produces $PGE_2$ and analogs thereof in relatively low overall yield. The other synthetic processes described in this reference are related to the Corey synthesis. Noyori, R. et al Angew. Chem., Int. Ed., Engl. 23, 847 (1984) describes a process which is triply convergent but not particularly efficient.

The various prior art processes use separate protective measures for the C-11 hydroxyl group and for insuring attachment of the requisite chain at C-8 of the cyclopentane ring in preparing the $PGE_2$ prostaglandins. A process has not been described by those skilled in the art wherein a protective group can be provided to protect the C-11 hydroxyl group and at the same time protect against undesirable reactions eminating from deprotonation at C-10 in a reactive cyclopentene intermediate containing 8–12 unsaturation by means of a cyclopentene intermediate having the formula:

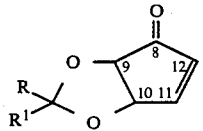

wherein R and R'C together with the C-10 oxygen provide a protective group.

Dugger at an American Chemical Society meeting in Washington, D.C. in September of 1983 (Abstract 129) discussed the preparation of an acetal protected optically active cyclopentanoid but found that the compounds were too difficult to obtain and abandoned the synthesis. The suggestion in the abstract was that various cyclopentanoid derivatives might be prepared from this intermediate, such as prostaglandins and carboxyclic nucleoside analogs, but no process for the synthesis was suggested or attempted because of the difficulty of such a process. Posternak, Th. in Helvetica Chemica Acta 55, 2839 to 2844 (1972) describes the preparation of a racemic mixture of the acetonide protected cyclopentanoid.

OBJECTS

It is therefore an object of the present invention to provide a process for the preparation of cyclopentanoids (I) which is much shorter and more efficient than prior art processes for the preparation of these compounds. Further it is an object of the present invention to provide novel intermediate compounds produced by the process of the present invention. These and other objects will become increasingly apparent by reference to the following description and the drawings.

IN THE DRAWINGS

FIGS. 1 to 3 are optical rotary dispersion (ORD) curves of intermediates and precursors thereof used in the process of the present invention.

GENERAL DESCRIPTION

The present invention relates to the process for the preparation of a cyclopentanoid (I) which comprises reacting in an organic solvent at a reduced temperature less than ambient temperatures a compound of the formula:

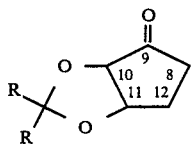

including stereoisomers wherein R and R'CO— provide a protecting group for the C-11 oxygen group and the C-10 methylene group and with a compound of the formula:

$R_\omega Cu$ wherein $R_\omega Cu$ is a copper complex soluble in the organic solvent wherein $R_\omega$ is selected from alkyl and alkenyl groups containing 4 to 12 carbon atoms to form an intermediate of the formula:

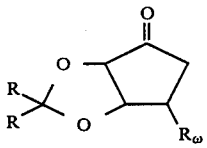

(II)

including stereoisomers; reacting II with $R_\alpha X$ in an organic solvent wherein $R_\alpha$ is selected from alkenyl and alkynyl ester, ketone and amide groups containing 3 to 12 carbon atoms and X is a halogen selected from chloro- and iodo- and bromo-groups to form a compound of the formula:

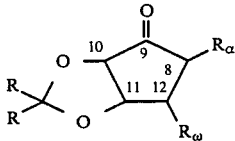

(III)

including stereoisomers; reacting (III) in an aqueous organic solvent mixture with a metallic reducing agent to produce a compound of the formula:

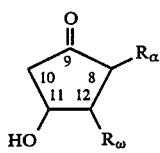

including stereoisomers as the cyclopentanoid (I).

In particular the present invention relates to a process for the preparation of a prostanoid (Ia) which comprises: reacting in an organic solvent at reduced temperatures between about −78° and 0° C. a compound of the formula:

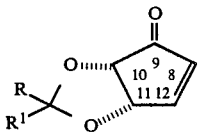

wherein R and R' are lower alkyl groups with a compound of the formula:

R$_\omega$Cu wherein R$_\omega$Cu is a stabilized copper butyl phosphine complex of the formula:

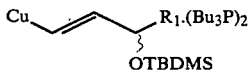

wherein R$_1$ is an alkyl group containing 1 to 8 carbon atoms and OTBDMS is a tert-butyldimethylsilyloxy group to produce an intermediate of the formula:

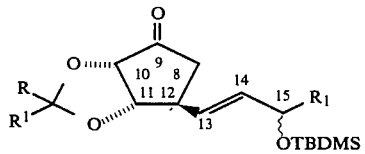

reacting II in an organic solvent at a temperature between about −30° and 0° C. with a compound of the formula: IR$_2$CO$_2$R$_3$ wherein —R$_2$CO$_2$R$_3$ is an alkenyl ester group and wherein R$_2$ contains 2 to 6 carbon atoms and R$_3$ is lower alkyl group containing 1 to 6 carbon atoms to produce a compound of the formula:

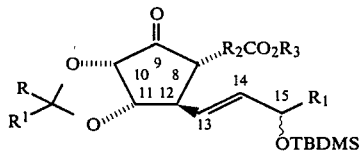

reacting III with an acid or salt in an organic solvent at a temperature between about −30° and 0° C. to produce a compound of the formula:

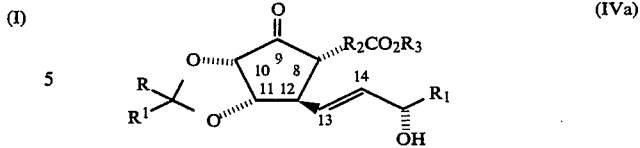

and reacting IV with an aluminum metal mercury amalgam as a metallic reducing agent in an aqueous organic solvent mixture at a temperature between about 0° and 70° C. to produce the prostaglandin of the formula:

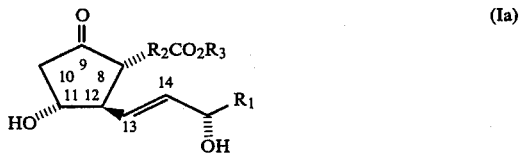

as the prostanoid (I).

The present invention also relates to novel intermediate compounds of the formula:

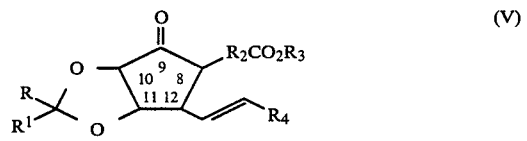

and stereoisomers thereof wherein R and R' are lower alkyl groups containing 1 to 6 carbon atoms, —R$_2$-CO$_2$R$_3$ is selected from an alkynyl and alkenyl ester groups, R$_2$ contains 3 to 10 carbon atoms, R$_3$ is a lower alkyl group which contains 1 to 6 carbon atoms, and R$_4$ is a hydroxyalkyl group containing 4 to 10 carbon atoms.

Finally the present invention relates to novel tertiary alkyl dimethyl silyloxy group containing compounds of the formula:

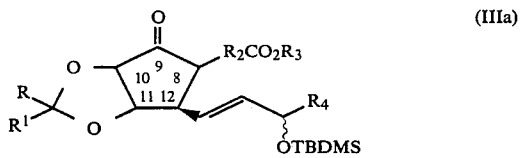

and stereoisomers thereof wherein R and R' are lower alkyl groups containing 1 to 6 carbon atoms, R$_1$ is an alkyl group containing 4 to 10 carbon atoms, —R$_2$-CO$_2$R$_3$ is selected from an alkenyl and alkynyl ester groups, R$_2$ contains 3 to 10 carbon atoms, R$_3$ is a lower alkyl group containing 1 to 6 carbon atoms and OTBDMS is a tertiary alkyl dimethyl silyloxy group.

R and/or R' can be hydrogen, lower alkyl containing 1 to 6 carbon atoms, preferably methyl; aryl, preferably phenyl; and aralkyl, preferably benzyl. R$_\alpha$ can be for instance: akenyl, alkynyl ester, ketone and amide groups containing 3 to 12 carbon atoms. Preferably R$_\alpha$ contains 7 carbon atoms in the chain without the ester group. The unsaturation can include dienes as well as acetylene and alkene functionality. R$_\omega$ can be for instance: alkyl and alkenyl groups containing 4 to 12 carbon atoms including arylalkyl and arylalkenyl groups which can be substituted functional groups particularly hydroxyl groups. $R_\omega$ can for instance be a butyl or pentyl group preferably containing as substituents hydroxyl and/or aryl or aryloxy groups.

SPECIFIC DESCRIPTION

The particular aim of the present invention was to develop a short, highly convergent route to prostanoids based on a conjugate-addition approach using enone 1 to 2 (Scheme 27). It was anticipated that cuprate addition followed by alkylation would result in trans-alkylated products 3 and 4 and that the presence of the 10-alkoxy substituent would suppress enolate equilibration, the major obstacle of this approach. A selective deoxygenation at the 10-position would furnish the PGE skeleton.

Scheme 27

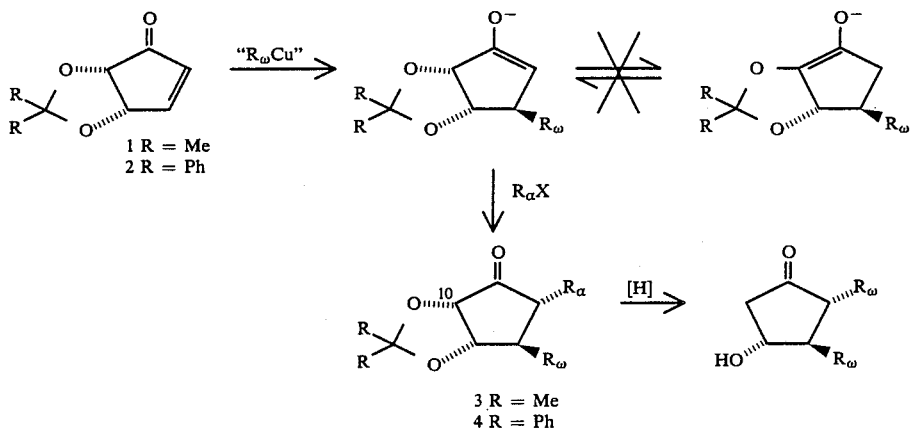

Scheme 29

SYMTHESIS OF PROTECTED 4,5-DIHYDROXY-2-CYCLOPENTEN-1-ONES

Cyclopentenone 1 has previously been prepared by a lengthy route from 2-cyclopentenone (Cocu, F. G., T. Posternak, Helv. Chim. Acta. 55, 2828, 2838 (1972)) (Scheme 28). Dugger (McDonald, C. E., R. W. Dugger, 186th National Meeting of the American Chemical Society, Washington, D.C., September 1983; American Chemical Society; Washington, D.C., ORGN 129 (1983)) has reported on attempts to prepare optically active 1 from ribose, but the key transformations were very unsatisfactory (Scheme 29) and 1 was not obtained in pure, characterizable form.

Scheme 28

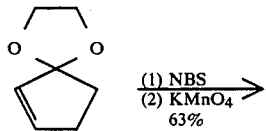

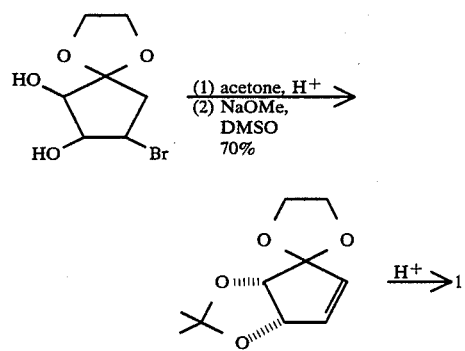

Enone 1 has been prepared from cyclopentadiene in six steps in an overall yield of 40% as shown in Scheme 30. Addition of photochemically generated singlet oxygen to cyclopentadiene and in situ reduction of the adduct with thiourea yielded cis-2-cyclopenten-1,4-diol (Kaneki, C., A. Sugimot and S. Tanaka, Synthesis 876 (1974)) which was acetylated with acetic anhydride to yield diacetate 5.

Scheme 30

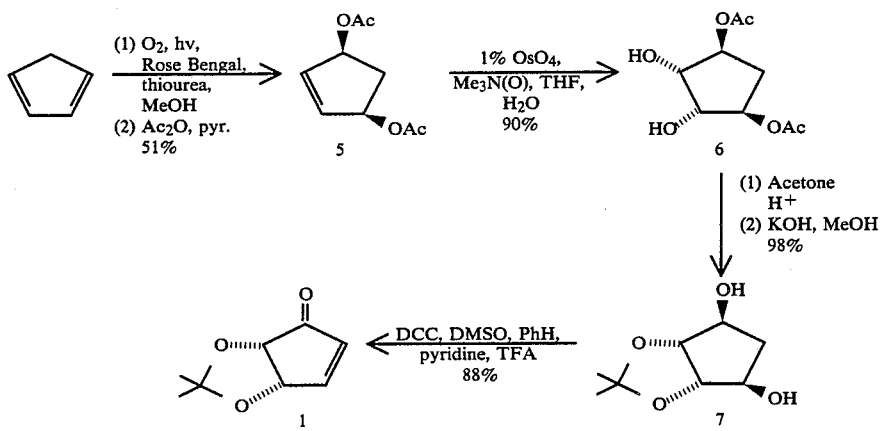

Scheme 30a

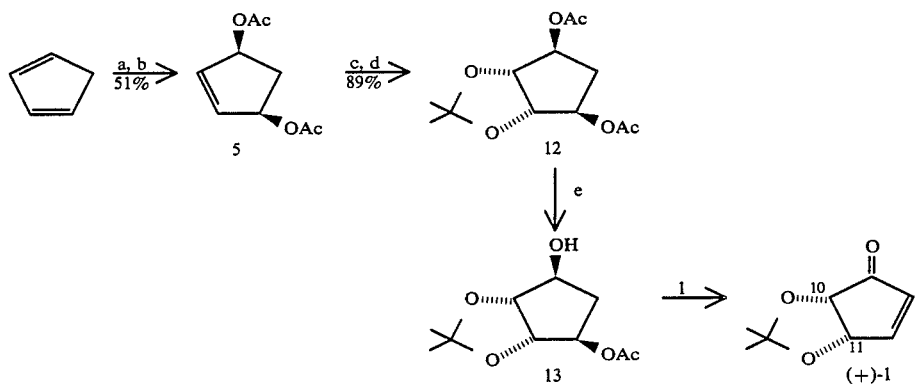

a(a) O₂, hv, rose bengal, thiourea, MeOH; (b) Ac₂O, pyridine, cat DMAP, CH₂Cl₂; (c) 1 mol % OsO₄, Me₃NO, THF, acetone, (d) acetone, cat TsOH; (e) electric eel acetylcholinesterase, H₂O, 25° C.; (i) CrO₃, H₂SO₄, acetone.

Based on earlier studies on enzymatic differentiation (Miura, S.; Kurozumi, S.; Toru, T.; Tanaka, T.; Kokayashi, M.; Matsubara, S.; Ishimoto, S. *Tetrahedron* 32, 1893, (1976); Laumen, K.; Schneider, M. *Tetrahedron Lett.* 5875 (1984)) of the acetates of meso-5, a number of esterase-catalyzed hydrolyses of meso-12 were examined. Success was variable until electric eel acetylcholinesterase was described in a recent report (Deardorff, D. R.; Matthews, A. J.; McMeekin, D. S.; Craney, C. L. *Tetrahedron Lett* 1255 (1986)) on the asymmetric hydrolysis of 5. Treatment of 12 in aqueous suspension with electric eel acetylcholinesterase (ca. 1 mg enzyme (Obtained from Sigma Chemical Co.)/g of 12) provided monoacetate 13 (80%) which was oxidized with Jones reagent to enone (+)-1 (95%, optical purity 98%) as shown in Scheme 30a.

The spectral characteristics of both the diol and 5 were identical to those reported in the literature (Kaneko, C., A. Sugimot and S. Tanaka, Synthesis 876 (1974)). Vicinal cis-hydroxylation of 5 from the least hindered side with 1 mole% osmium tetroxide and trimethylamine N-oxide (VanRheene, V., R. C. Kelly and D. Y. Cha, Tetrahedron Lett. 1973 (1976)) as reoxidant furnished diol 6 in 90% yield. Alternately, this oxidation could be accomplished in 71% yield with potassium permanganate under biphasic conditions (Kunnen, K. B., Dissertation, Wayne State University, Detroit, Mich. (1985)). Acid-catalyzed ketalization of 6 with acetone followed by acetate hydrolysis with potassium hydroxide gave diol 7 in 98% yield. The acetates could also be removed by treatment with lithium aluminum hydride (LAH), but the yield was slightly lower and the method was substantially more expensive. Oxidation/dehydration of 5 was best carried out with the Moffatt oxidation (Pfitzner, K. R., J. G. Moffatt, J. Am. Chem. Soc. 87, 5661, 5670 (1965)) to produce 1 in 88% yield after chromatography to remove the dicyclohexylurea byproduct. This oxidation could also be achieved using chromium trioxide/pyridine complex in pyridine (Sarett's reagent) (Poos, G. I., G. E. Arth, R. E. Beyler and L. H. Sarett, J. Am. Chem. Soc. 75, 422 (1953)). Although no chromatography was required, the yields were slightly lower (70%) and the workup was more difficult. Oxidation of 7 with Jones reagent (Bowden, K., I. M. Heilbron, E. R. Jones and B. C. Weedon, C. J. Chem. Soc. 39 (1946)) gave β-hydroxyketone 8 in 85% yield without removal of the acetonide. Ketone 8 could be smoothly dehydrated with

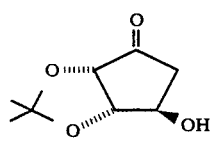

8 acetic anhydride to produce 1 quantitatively. The six-step synthesis of 1 required only one chromatography—all other intermediates were purified by distillation or recrystallization.

A number of analogues of 1 utilizing different diol protecting groups were examined, including 2, which was synthesized in an analogous manner as 1 (Scheme 31).

Scheme 31

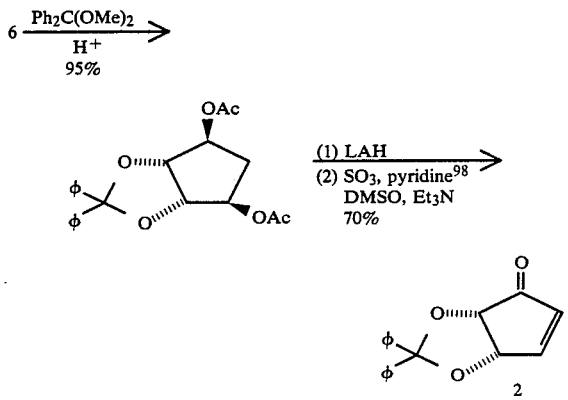

This invention focused only on 1 and 2 as potential prostaglandin precursors. Since it was ultimately desired to synthesize prostaglandins in enantiomerically pure form, enones 1 and 2 were required in optically pure form. This was achieved by an optical resolution of the ketones based on sulfoximine chemistry (Johnson, C. R., and J. R. Zeller, J. Am. Chem. Soc. 104, 4021 (1982)). Addition of the lithium anion of optically pure sulfoximine (+)-9 to enone 1 stereospecifically from the convex face furnished only two diastereomeric adducts by HPLC analysis, the faster eluting 10-I and 10-II (Scheme 32). These diastereomers were separated on preparative scale Scheme 32

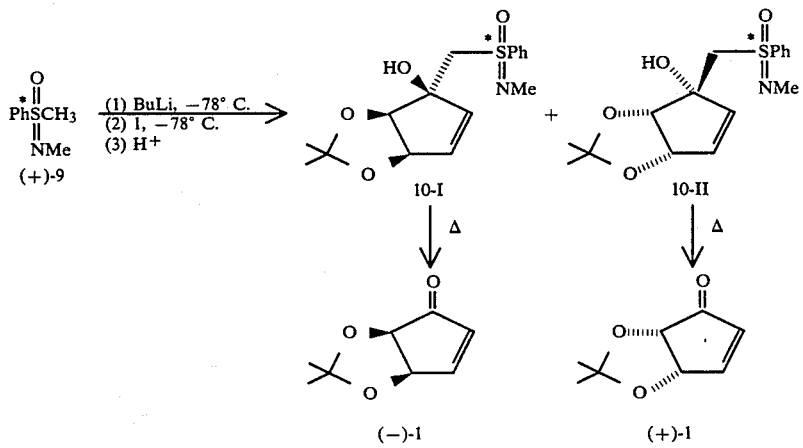

by flash chromatography ($\alpha$-1.37) to give a 42% yield of 10-I with $[\alpha]_D^{25} -94.3°$ (c 1.19, CHCl$_3$) and a 34% yield of 10-II with $[\alpha]_D^{25} +111.8°$ (c 1.055, CHCl$_3$). Thermolysis in refluxing toluene of 10-I and 10-II, separately, furnished (−)-1 with $[\alpha]_D^{25} -70.8°$ (c 0.925, CHCl$_3$) and (+)-1 with $[\alpha]_D^{25} +71.8°$ (c 0.91, CHCl$_3$) respectively, along with recovered sulfoximine (+)-9 which could be recycled. Addition of the anion of (+)-9 to enone 2 also gave only two diastereomers. The selectivity factor ($\alpha$) was again fairly small (1.41) for the two diastereomers.

The racemic mixtures of the enone 1 can be used in preparing the prostanoids. However, the optically active form (+)-1 derivatives are more active pharmacologically and thus they are described hereinafter.

The absolute configurations of (−)-1 and (+)-1 were determined by comparison of their optical rotatory dispersion (ORD) curves with that of a similar optically pure compound of known absolute configuration, (−)-11. This enone had been synthesized from

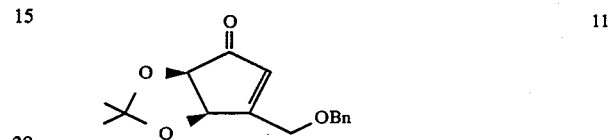

5-O-benzyl-D-ribonolactone and had been used in the synthesis of (−)-neplanocin A (Lim, M, I, V. E. Marquez, Tetrahedron Lett. 5559 (1983)). The ORD curve of (−)-11 exhibited a positive Cotton effect (FIG. 1). The ORD curve of (−)-1 also showed a positive Cotton effect (FIG. 2), while (+)-1 exhibited a negative Cotton effect (FIG. 3). Since (−)-1 and (−)-11 both exhibited a positive Cotton effect, they should have the same absolute configuration. Enone (+)-1 exhibited a negative Cotton effect, hence it should have the opposite absolute configuration of (−)-1 and (−)-11. The positive optical rotation that Dugger (McDonald, C. E., R. W. Dugger, "Abstract of Papers," 186th National Meeting of the American Chemical Society, Washington, D.C., September 1983, ORGN 129 (1983); Dugger, R. W., Miami University, Ohio, personal communication, 1985) obtained for optically active 1 substantiated the assignment of absolute configuration, although Dugger's rotation was substantially lower than the rotation of resolved (+)-1 ($[\alpha]_D+8°$ vs. $[\alpha]_D+71.8°$). Ultimately, the absolute configuration of (+)-1 was proven by its conversion into (−)-PGE$_2$ methyl ester (vide infra).

Since the PGEs have an 11R-hydroxy group, the enone with the (4S,5S) configuration ((+)-1) was the enone needed for a synthesis of a PGE.

cis-2-Cyclopenten-1,4-diol

A 4 L photochemical reaction vessel, equipped with a water-jacketed immersion well, was charged with methanol (4 L), freshly prepared cyclopentadiene (35 mL, 0.425 mol), thiourea (22 g, 0.289 mol), and rose bengal (0.40 g). After bubbling oxygen through the mixture for 5 min, irradiation was begun with a 450 W tungsten-halogen lamp. After 3 h of vigorous stirring, the oxygen flow and the irradiation were terminated and the suspension allowed to stir in the dark for 16 hours. Methanol was removed by rotary evaporation, and the resulting slurry was diluted with water (200 mL) and filtered. The filtrate was concentrated by rotary evaporation and the brown oil distilled (106°–107° C./0.4 torr) to yield cis-2-cyclopenten-1,4-diol as a colorless oil (22.70 g, 53%): IR (neat) 3600, 3350 (br), 3060, 2995, 2935, 1400, 1235, 1110, 1060 (s), 995 (s), 870 cm$^{-1}$; $^1$H NMR (CDCl$_3$) 5.98 (s, 2H), 4.62 (dd, $J_1=7$ Hz, $J_2=4$ Hz, 2H), 3.81 (br, 2H), 2.69 (dt, $J_1=14$ Hz, $J_2=7$ Hz, 1H), 1.53 (dt, $J_1=14$ Hz, $J_2=4$ Hz, 1H). This data agrees with published values.

cis-3,5-Diacetoxycyclopentene (5)

cis-2-Cyclopenten-1,4-diol (46.0 g, 0.459 mol), pyridine (112 mL, 1.385 mol), and acetic anhydride (130 mL, 1.375 mol) were dissolved in dichloromethane (600 mL) and cooled to 0° C. 4-(N,N-Dimethylamino)-pyridine (0.60 g) was added, the ice bath was removed, and the mixture was stirred at room temperature for 13 h. The mixture was poured into a separatory funnel and washed successively with two 200-mL portions of 3N HCl, saturated aqueous NaHCO$_3$ (200 mL), and saturated aqueous NaCl (200 mL). The organic layer was dried over Na$_2$SO$_4$ and concentrated by rotary evaporation. Distillation (80°–81° C./0.9 torr; lit 110°–112° C./8 torr) provided a colorless oil (81.50 g, 96.4%): IR (neat) 3070 (w), 2990, 2945, 1740 (s), 1430, 1365 (s), 1230 (s), 1120, 1070, 1015, 985, 950, 900, 770 cm$^{-1}$; $^1$H NMR (CDCl$_3$) δ 5.93 (s, 2H), 5.38 (dd, $J_1=7.4$ Hz, $J_2=3.8$ Hz, 2H), 2.73 (ddt, $J_1=14.9$ Hz, $J_2=7.5$ Hz, $J_3=1.3$ Hz, 1H), 1.90 (s, 6H), 1.57 (dt, $J_1=14.9$ Hz, $J_2=3.8$ Hz, 1H); $^{13}$C NMR (CDCl$_3$) δ 170.00, 134.18, 76.14, 36.72, 20.53. This data agrees with literature values.

(1α,2α,3β,5β)-3,5-Diacetoxy-1,2-cyclopentanediol (6)

cis-3,5-Diacetoxycyclopentene (5) (81.0 g, 0.440 mol) and osmium tetroxide (1.0 g, 3.90 mmol) were stirred in THF (800 mL) and acetone (300 mL). A solution of trimethylamine N-oxide dihydrate (59.0 g, 0.530 mol) in water (90 mL) was added. The mixture was stirred at room temperature for 15 h. The THF and acetone were removed by rotary evaporation, and the aqueous mixture was poured into a separatory funnel containing saturated aqueous NaHSO$_3$ (100 mL). The aqueous layer was extracted with ten 100-mL portions of ethyl acetate. The combined extracts were dried over Na$_2$SO$_4$ and concentrated by rotary evaporation. Recrystallization yielded a white solid (85.9 g, 89.5%): mp 97.5°–98.5° C.; IR (CHCl$_3$) 3530 (br), 3030, 3010, 2940, 1730 (s), 1370 (s), 1255 (s), 1100, 1080, 1040 (s), cm$^{-1}$; $^1$H NMR (CDCl$_3$) δ 4.97 (p, J=3.8 Hz, 2H), 4.12 (m, 2H), 3.86 (br, 2H), 2.79 (dt, $J_1=15.4$ Hz, $J_2=7.8$ Hz, 1H), 2.09 (s, 6H), 1.66 (dt, $J_1=15.4$ Hz, $J_2=4.4$ Hz, 1H); $^{13}$C NMR (CDCl$_3$) δ 171.19, 77.90, 75.78, 33.76, 20.79. This data agrees with published values.

4β,6-Diacetoxy-2,2-dimethyl-3aβ,5,6α,6aβ-tetrahydro-4H-cyclopenta-1,3-dioxole Diol 6 (20.0 g, 91.7 mmol) and p-toluenesulfonic acid hydrate (TsOH.H$_2$O, 250 mg) were dissolved in dry acetone (1.5 L) and stirred for 60 h. The mixture was concentrated by rotary evaporation and the residue was dissolved in diethyl ether (300 mL), washed with water (100 mL), dried over Na$_2$SO$_4$, and concentrated by rotary evaporation to provide a white, crystalline solid (23.4 g, 99%): mp 79.5°–80.5° C.; IR (CHCl$_3$) 2985 (w), 2930 (w), 1735 (s), 1375 (s), 1240 (s), 1155, 1050 (s), 855 cm$^{-1}$; $^1$H NMR (CDCl$_3$) δ 5.08 (dd, $J_1=5.6$ Hz, $J_2=1.3$ Hz, 2H), 4.62 (d, J=1.5 Hz, 2H), 2.41 (dt, $J_1=15.7$ Hz, $J_2=5.5$ Hz, 1H), 2.05 (s, 6H), 1.96 (dt, $J_1=15.7$ Hz, $J_2=1.5$ Hz, 1H), 1.44 (s, 3H), 1.28 (s, 3H); $^{13}$C NMR (CDCl$_3$) δ 169.74, 110.97, 84.09, 78.41, 34.07, 26.11, 23.75, 20.85. This data agrees with literature values.

2,2-Dimethyl-3aβ,5,6α,6aβ-tetrahydro-4H-cyclopenta-1,3-dioxol-4β,6-diol (7)

A solution of NaOH (17.0 g, 303 mmol) in MeOH (400 mL) was added to a solution of 22 (34.0 g, 132 mmol) in MeOH (700 mL) and the mixture was stirred for 30 min. The reaction mixture was adjusted to pH 8 with 1N HCl (250 mL) and concentrated on a rotary evaporator to a volume of 300 mL. The solution was extracted with six 100-mL portions of diethyl ether. The combined ether extracts were dried over Na$_2$SO$_4$, and concentrated by rotary evaporation. Recrystallization from CCl$_4$ yielded a white, crystalline solid (22.7 g, 99%): mp 135°–136° C.; IR (CHCl$_3$) 3600, 3440 (br), 2980 (s), 2930 (s), 1420, 1385 (s), 1375 (s), 1260, 1155 (s), 1065 (s), 1045 (s), 960, 910, 860 (s), cm$^{-1}$; $^1$H NMR (CDCl$_3$) δ 4.65 (d, J=1.8 Hz, 2H), 4.25 (dd, $J_1=6.6$ Hz, $J_2=4.4$ Hz, 2H), 2.82 (d, J=6.8 Hz, 2H), 2.15 (dt, $J_1=14.6$ Hz, $J_2=4.4$ Hz, 1H), 1.87 (dt, $J_1=14.7$ Hz, $J_2=1.7$ Hz, 1H), 1.43 (s, 3H), 1.32 (s, 3H); $^{13}$C NMR (CDCl$_3$) δ 110.2, 86.1, 77.6, 37.1, 25.9, 23.6. This data agrees with published values.

2,2-Dimethyl-3aβ,6aβ-dihydro-4H-cyclpenta-1,3-diox-ol-4-one (1)

Diol 7 (3.48 g, 20 mmol) was dissolved in dry benzene (80 mL) and dry DMSO (80 mL). Pyridine (2.4 mL, 30 mmol), trifluoroacetic acid (1.2 mL, 15 mmol), and 1,3-dicyclohexylcarbodiimide (DCC, 18.5 g, 90 mmol) were added in order, and the reaction mixture was stirred for 18 h. The mixture was filtered, and the filtrate washed with three 100-mL portions of water, dried over Na$_2$SO$_4$, and concentrated on a rotary evaporator. Flash chromatography using 10:1 hexane/EtOAc followed by recrystallization from pentane gave a white solid (2.70 g, 88%); mp 37.5°–38.5° C. (lit mp 36°–38° C.); IR (CHCl$_3$) 3020, 2990, 2930, 1725 (s), 1590 (w), 1455 (w), 1385 (s), 1375 (s), 1345, 1230, 1185, 1150, 1095 (s), 1065, 960, 910, 850 cm$^{-1}$; $^1$H NMR (CDCl$_3$) δ 7.63 (dd, $J_1=6.0$ Hz, $J_2=2.3$ Hz, 1H), 6.24 (dd, $J_1=6.0$ Hz, $J_2=0.5$ Hz, 1H), 5.29 (ddd, $J_1=5.5$ Hz, $J_2-2.3$ Hz, $J_3=0.65$ Hz, 1H), 4.49 (d, J=5.5 Hz, 1H), 1.43 (s, 6H). This data agrees with literature values.

6-Hydroxy-2,2-dimethyl-3aβ,5,6α,6aβ-tetrahydro-4H-cyclpenta-1,3-dioxol-4-one (8)

Diol 7 (0.15 g, 0.86 mmol) was stirred in acetone (10 mL) and 1.25M Jones reagent (0.8 mL, 1.0 mmol) was added. The reaction mixture was stirred for 1 h, poured into saturated aqueous NaHSO$_4$ (10 mL), and extracted with three 20-mL portions of diethyl ether. The combined ether extracts were washed with water (30 mL), dried over Na$_2$SO$_4$, and concentrated on a rotary evaporator to give a colorless oil (0.126 g, 85%): $^1$H NMR (CDCl$_3$) δ 4.65 (d, J=5.3 Hz, 1H), 4.50 (d, J=5.3 Hz, 1H), 4.36 (d, J=5.3 Hz, 1H), 3.28 (br, 1H), 2.87 (ddd, J$_1$=18.4 Hz, J$_2$=5.3 Hz, J$_3$=0.5 Hz, 1H), 2.29 (dd, J$_1$=18.3 Hz, J$_2$=1.0 Hz, 1H), 1.43 (s, 3H), 1.37 (s, 3H).

Reaction of (+)-N,S-Dimethyl-S-phenylsulfoximine ((+)-9) with (±)-1;2,2-Dimethyl-4-(N-methylphenylsulfonimidoylmethyl)-3aβ-6aβ:dihydro-4H-cyclopenta-1,3-dioxol-4α-ol (10)

A solution of n-BuLi in hexane (1.6M) was added to a solution of (+)-9 (2.54 g, 15.0 mmol, 99.5% ee) and triphenylmethane (10 mg) in dry THF (100 mL) at 0° C. until an orange color persisted. The solution was stirred at 0° C. for 15 min and cooled to −78° C. Enone (±)-1 (2.31 g, 15.0 mmol) in dry THF (25 mL) was added slowly, and the reaction mixture was stirred at −78° C. for 1 h. The cold reaction mixture was poured into ether (50 mL) and saturated aqueous NH$_4$Cl (50 mL) in a separatory funnel. The layers were separated and the aqueous layer extracted twice with ether (50 mL). The combined ether extracts were dried over Na$_2$SO$_4$ and concentrated by rotary evaporation to yield a colorless gum. Analytical HPLC (65% EtOAc/35% hexane; 2 mL/min flow rate) showed two diastereomers (retention times 11.2 min and 14.7 min; ratio=1.1/1; α=1.37) which were separated by very careful flash chromatography with 2:1 hexane/EtOAc to give 2.02 g of the faster eluting diastereomer I and 1.67 g of diastereomer II (76%). Diastereomer I was a white solid: mp 71°–73° C.; $^1$H NMR (CDCl$_3$ δ 7.80 (d, J=7.1 Hz, 2H), 7.53 (m, 3H), 5.81 (d, J=5.7 Hz, 1H), 5.66 (d, J=5.7 Hz, 1H), 5.65 (br, 1H), 5.07 (s, 2H), 3.55 (d, J=14.3 Hz, 1H), 3.06 (d, J=14.3 Hz, 1H), 2.56 (s, 3H), 1.38 (s, 3H), 1.36 (s, 3H); $^{13}$C NMR (CDCl$_3$) δ 136.96, 132.92, 132.88, 129.26, 128.98, 112.61, 83.68, 80.79, 62.43, 28.89, 27.47, 26.55; [α]$_D^{25}$ −94.3° (c 1.19, CHCl$_3$, corrected for 99.5% pure (+)-9. Anal. calcd for C$_{16}$H$_{21}$NO$_4$S: C, 59.42; H, 6.55. Found: C, 59.42; H, 6.92. Diastereomer II was a white solid: mp 73°–75° C.; $^1$H NMR (CDCl$_3$) δ 7.85 (d, J=6.7 Hz, 2H), 7.56 (m, 3H), 6.03 (d, J=5.8 Hz, 1H), 5.88 (dd, J$_1$=5.8 Hz, J$_2$=1.4 Hz, 1H), 5.53 (br, 1H), 4.98 (d, J=5.3 Hz, 1H), 4.54 (d, J=5.4 Hz, 1H), 3.45 (d, J=14.1 Hz, 1H), 3.22 (d, J=14.1 Hz, 1H), 2.61 (s, 3H), 1.41 (s, 3H), 1.33 (s, 3H); $^{13}$C NMR (CDCl$_3$) δ 137.32, 133.01, 132.00, 129.31, 129.08, 112.86, 83.12, 81.61, 79.99, 63.31, 28.94, 27.39, 26.45; [α]$_D^{25}$ +111.8 (c 1.055, CHCL$_3$, corrected for 99.5% pure (+)-9). Anal. calcd for C$_{16}$H$_{21}$NO$_4$S: C, 59.42; H, 6.55. Found: C, 59.16; H, 6.93.

The Thermolysis of 10

A solution of β-hydroxysulfoximine (−)-10-I (1.97 g, 6.09 mmol) in dry toluene (100 mL) was refluxed for 9 h. Concentration by rotary evaporation and flash chromatography with 6:1 hexane/EtOAc provided 0.91 g (97%) of (−)-2,2-dimethyl-3aβ,6aβ-dihydro-4H-cyclopenta-1,3-dioxol-4-one ((−)-1) as a white solid with [α]$_D^{25}$ −70.8° (c 0.925, CHCl$_3$). In an identical manner (+)-10-II (1.62 g, 5.01 mmol) was thermolyzed to give 0.755 g (98%) of (+)-1 as a white solid with [α]$_D^{25}$ +71.8° (c 0.91, CHCl$_3$). The dextrorotatory enantiomer was assigned the (3aS, 6aS) configuration and the levorotatory enantiomer was assigned the (3aR, 6aR) configuration based on a comparative ORD study with (−)-11.

Scheme 30b

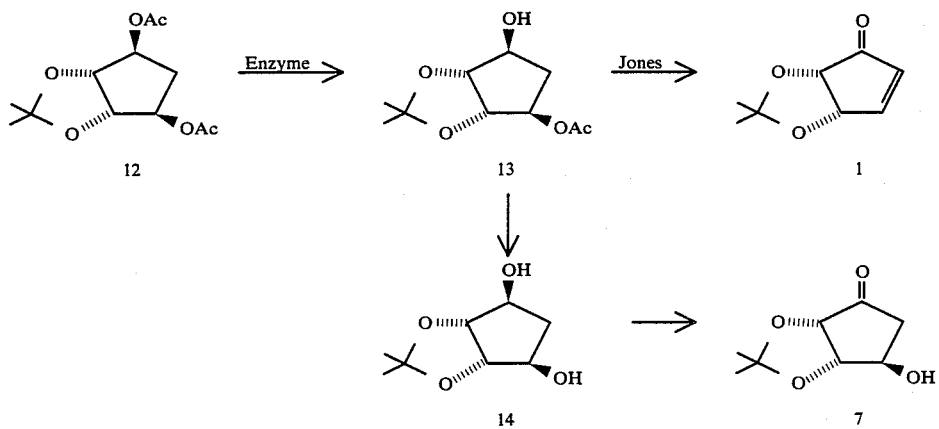

Enzymatic Semi-hydrolysis of meso-4β,6-Diacetoxy-2,2-dimethyl-3aβ,5,6a,6aβ-tetrahydro-4H-cyclopenta-1,3-dioxole (12) and Conversion of the Resulting Monoacetate (13) to (+)-(3aS,6aS)-2,2-Dimethyl-3aβ,6aβ-dihydro-4H-cyclopenta-1,3-dioxol-4-one (1). As shown in Scheme 30b, the finely powdered meso-diacetate 5 (12.9 g, 50 mmol) was stirred in 425 mL of a 0.58M aqueous phosphate pH 6.9 buffer solution. Sodium azide (42 mg) and electric eel acetylcholinesterase (15 mg) were added, and the heterogeneous solution was stirred at 25° C. for 19 h. The nearly homogeneous reaction mixture was extracted with diethyl ether (5×100 mL), and the combined ether extracts were dried over Na$_2$SO$_4$ and concentrated by rotary evaporation. The colorless semi-solid was flash chromatographed using first 5:1 hexane/EtOAc, then 1:1 hexane/EtOAc, to provide (3aS, 4R, 6S, 6aR)-4β-acetoxy-2,2-dimethyl-6-hydroxy-3aβ,5,6a,6aβ-tetrahydro-4H-cyclopenta-1,3-dioxole (12) as a white solid (8.5 g, 79%): $^1$H NMR (CDCl$_3$) δ 5.05 (d, J=5.2 Hz, 1H), 4.58 (dd, J$_1$=5.7 Hz, J$_2$=1.1 Hz, 1H), 4.52 (d, J=5.7 Hz, 1H) 4.18 (br, 1H), 2.67 (br, 1H), 2.28 (dt, J$_1$=15.2 Hz, J$_2$=5.3 Hz, 1H), 2.01 (s, 3H), 1.81 (dt, J$_1$=15.2 Hz, J$_2$=1.5 Hz), 1.35 (s, 3H), 1.21 (s, 3H); $^{13}$C NMR (CDCl$_3$ δ 169.78, 110,61, 86.08, 84.17, 79.35, 76.43, 36.19, 26.07, 23.71, 20.94; [α]$_D^{25}$ −12.74° (c 0.95, CHCl$_3$). Anal. calcd. for $C_{10}H_{16}O_5$: C, 55.55; H, 7.46; Found: C, 55.64; H, 7.53. Also isolated was the diol (13) (1.25 g, 14%) (which could be reconverted to the diacetate and recycled) along with 0.63 g (5%) of recovered starting diacetate (5).

The monoacetate (12) (8.3 g, 38.4 mmol) was dissolved in 450 mL of acetone and cooled to 0° C. Jones reagent (22.1 mL of a 1.35M solution, 29.6 mmol; (Jones reagent: $CrO_3$ (13.4 g, 0.134 mol) dissolved in 12 mL of concentrated sulfuric acid and diluted with distilled water to 100 mL) was added, and the reaction mixture was stirred at 0° C. for 15 min and at 25° C. for 4 h. Solid $NaHCO_3$ (1 g) and $NaHSO_3$ (1 g) were added and the solution was filtered. The colorless solution was concentrated by rotary evaporation, and the crude product was dissolved in diethyl ether (200 mL), and the solution was washed with saturated NaCl (150 mL). The layers were separated, and the aqueous layer was washed with 100 mL of diethyl ether. The combined ether extracts were dried over $Na_2SO_4$ and concentrated by rotary evaporation. Flash chromatography, first with 5:1 hexane/EtOAc, then with 2:1 hexane/EtOAc, provided the title enone (1) as a white crystalline solid (5.65 g, 95%): $[\alpha]_D^{25}$ +70.49° (c 0.915, $CHCl_3$) (98%ee) along with recovered monoacetate (12) (0.35 g, 4%).

Alternately, it was found to be efficient to oxidize the monoacetate 13 as a mixture containing the diol (14). Jones oxidation provided the (+)-enone (1) along with related dl-β-hydroxy ketone (7), which were easily separated by flash chromatography using 5:1 hexane/EtOAc and can be dehydrated to produce (1).

THE SYNTHESIS OF (±)-PGE$_2$ METHYL ESTER

1. Cuprate Addition

For maximum efficiency, mixed homocuprates and organocopper reagents, in which only one equivalent of the valuable ω side-chain is employed, were prepared. An extensive cuprate study was carried out by SiH, who found that two of the more successful reagents were Corey's mixed cuprate 55 and a stabilized organocopper reagent 56, which both gave addition products in yields of 50–55%. A brief cuprate study was undertaken using vinyllithium 51, which was generated from the

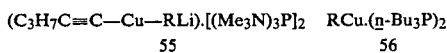
55    56 vinylstannane 49 immediately before use as previously described. Initially, the addition product 57 was isolated as a mixture of two diastereomers by a very difficult flash chromatography, due to the presence of byproducts with similar retention times. Silyl ether 57 was easily deprotected with catalytic potassium carbonate in methanol (eq 22) to quantitatively provide 58 as an inseparable mixture of two diastereomers.

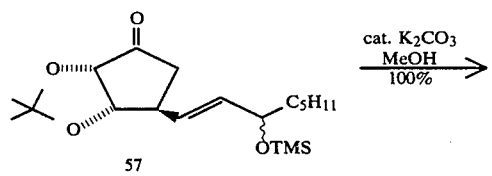

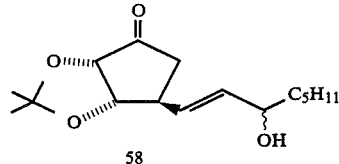
58

It was found to be much more advantageous (higher yields and easier chromatography) to treat the crude cuprate reaction mixture with potassium carbonate in methanol followed by flash chromatography to furnish 58. The various organocopper reagents used and the yields obtained with each are shown in eq 23–26.

Copper(I) iodide/tributylphosphine complex was found to be a very convenient form of copper (I) for these reactions. The complex is soluble in THF and diethyl ether, the phosphine stabilizes the vinylcuprate, resulting in a much cleaner reaction, and the workup is much easier since all the copper salts remain in solution.

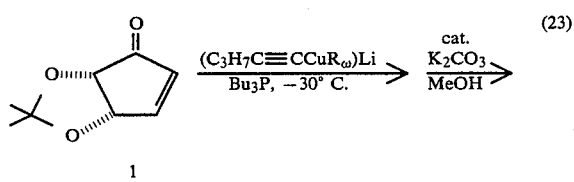

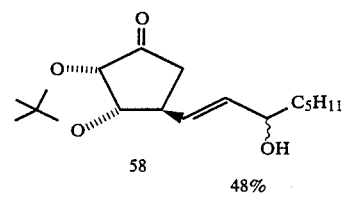

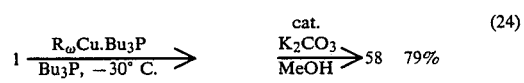

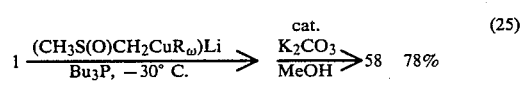

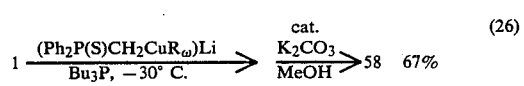

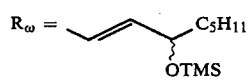

Also, the tributylphosphine can easily be removed by flash chromatography.

The mixed cuprate shown in eq 23 was generated by an addition of 1-pentynyllithium to copper(I) iodide/tributylphosphine complex followed by the addition of vinyllithium 51. To the resulting slurry was added enone (±)-1. Addition was complete after 1 h at −30° C. to provide the product (58) in 48% yield after deprotection and chromatography.

The stabilized organocopper reagent shown in eq 24 was easily formed by reaction of vinyllithium 51 with the copper(I)-phosphine complex with an additional equivalent of the phosphine. Addition of the colorless, homogeneous solution to enone (±)-1 and stirring for 1 h at −30° C. produced, after deprotection and purification, 58 in 79% yield.

Considerable effort in our laboratory has been devoted to the development of mixed organocuprates with novel non-transferable ligands. Two very promising examples were explored in our cuprate addition reaction. The lithium anion of dimethyl sulfoxide was added to the same copper(I)-phosphine complex followed by addition of the vinyllithium 51. Addition to enone (±)-1, deprotection, and chromatography as previously described furnished 58 in 78% yield (eq 25). The DMSO could easily be removed in workup by washing with water.

The second novel mixed cuprate, shown in eq 26, was prepared from the lithium anion of methyldiphenylphosphine sulfide, copper(I) iodide/tributylphosphine complex, and vinylllithium 51. Addition to enone (±)-1, followed by deprotection and chromatography, provided 58 in 67% yield. When this same reaction was carried out in the absence of tributylphosphine (use of cuprous iodide instead of the phosphine complex), a 10% decrease in yield was noted (57% yield). When vinyllithium reagent 52 was used in these cuprate addition reactions the yield increased significantly. The two organocopper reagents which gave the highest yields of addition in the above study were repeated using the t-butyldimethylsilyl protected 52 instead of 51. The stabilized organocopper reagent (eq 27) furnished a 93% yield of 59 as an inseparable mixture of two diastereomers, and the mixed homocuprate from dimethyl sulfoxide provided an 89% yield of 59 (eq 28). The reactions using the t-butyldimethylsilyl-protected ω side-chain were not only higher yielding, but were also much cleaner than the corresponding trimethylsilyl-protected cases. Because of the high yield of addition and because of its ease of preparation, the stabilized organocopper compound shown in eq 27 was used in the actual prostaglandin synthesis. Since the t-butyldimethylsilyl group is not removed as easily as the trimethylsilyl group, the problem of selective removal of the protecting group eventually had to be addressed.

The yields obtained in these cuprate additions were generally significantly higher than those previously described in literature.

THE SYNTHESIS OF (−)-PGE$_2$ METHYL ESTER

Optically pure (−)-PGE$_2$ methyl ester ((−)-69) was synthesized as described in Scheme 40. Addition of the stabilized organocopper reagent derived from (−)-48 to the resolved ketone (+)-1, followed by alkylation with an excess of iodide 34 in the presence of HMPA (hexamethyl phosphonic triamide)

Scheme 40

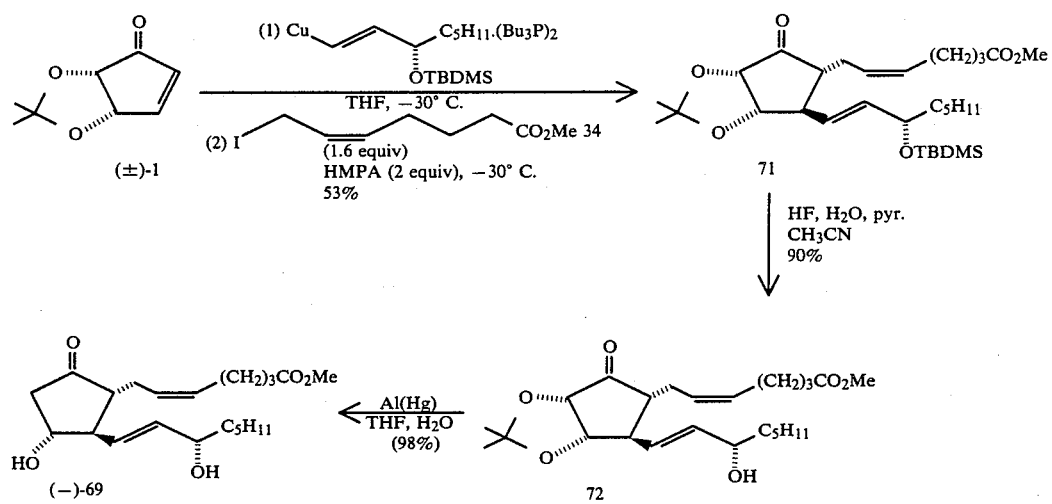

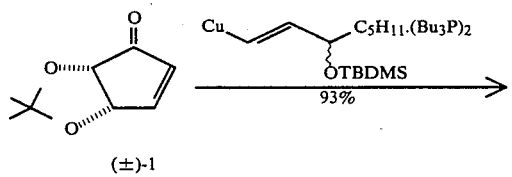

provided, after flash chromatography, a 46% yield of 71 [[α]$_D^{25}$ +7.55° (c 0.98, CHCl$_3$)] as a single diastereomer by $^{13}$C NMR. The unalkylated product 73 with [α]$_D^{25}$ +102.2° (c 1.15, CHCl$_3$) was isolated in 25% yield. This product was separately alkylated, but the purity of product 71 was somewhat lower than desired. A minor amount of impure cis-alkylation product 74 was isolated. This was equilibrated to a 2:1 mixture of 71 and 74 with catalytic sodium acetate in refluxing

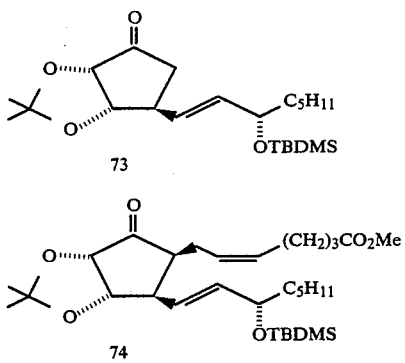

methanol to provide another 7% of 71 after flash chromatography. Alkylation product 71 was thus obtained in 53% overall yield.

Desilylation of 71 with 5:1 aqueous HF (50%)/pyridine in acetonitrile at 25° C. for 4.5 h afforded a 78% yield (90% based on recovered starting material) of alcohol 72 $[[\alpha]_D^{25} -0.52°$ (c 2.29, CHCl$_3$)] along with a 14% yield of recovered 71. If the reaction time was increased in an attempt to allow the reaction to go to completion, the removal of the acetonide started to become a problem.

Aluminum amalgam reduction of 72 with four portions of Al(Hg) over a period of 37 h provided after flash chromatography an 89% yield (98% based on recovered starting material) of (−)-PGE$_2$ methyl ester ((−)-69) along with 9% of recovered 72. By TLC, $^1$H and $^{13}$C NMR, and IR, (−)-69 was identical to the previously prepared (±)-PGE$_2$ methyl ester ((±)-69), thus confirming the structural assignment of (±)-69.

Noyori (Suzuki, M., T. Kawagishi and R. Noyori, Tetrahedron Lett., 5563 (1982), Also see, Suzuki, M., Yanagisawa, A. and R. Noyori, ibid. 1384 (1984)) has reported a synthesis of (−)-PGE$_2$ methyl ester with $[\alpha]_D^{20} -71.7°$ (c 1.04, MeOH), while an authentic sample he prepared by the esterification of commercial (−)-PGE$_2$ with diazomethane had $[\alpha]_D^{20} -71.1°$ (c 1.56, MeOH). Ester (−)-69 was obtained with $[\alpha]_D^{20} -71.8°$ (c 1.25, MeOH). Since the ester hydrolysis had been previously carried out enzymatically, (Sih, C. J., J. B. Heather, R. Sood, P. Price, G. Peruzzoti, L. H. Lee and S. S. Lee, J. Am. Chem. Soc. 97, 865, (1975)) this represented a total synthesis of (−)-PGE$_2$.

This synthesis represents one of the shortest routes to (−)-PGE$_2$, and one of only two (the other approach is described in Suzuki, M., et al., J. Am. Chem. Soc., 107, 3348 (1985)) successful three-component coupling approaches employing a direct alkylation. Since it is highly convergent, this approach is applicable towards the synthesis of other prostaglandin analogues.

SYNTHESIS OF THE α SIDE-CHAIN

Iodide 34 was synthesized (Scheme 37) using a modification of an approach described by Corey (Corey, E. J., et al., J. Am. Chem. Soc., 95, 8483 (1973)). The lithium anion of propargyl tetrahydropyranyl ether was alkylated with 1-bromo-3-chloropropane to give chloride 35. Displacement of chloride with cyanide ion yielded nitrile 36 which was hydrolyzed with sodium hydroxide to produce acid 37.

Scheme 37

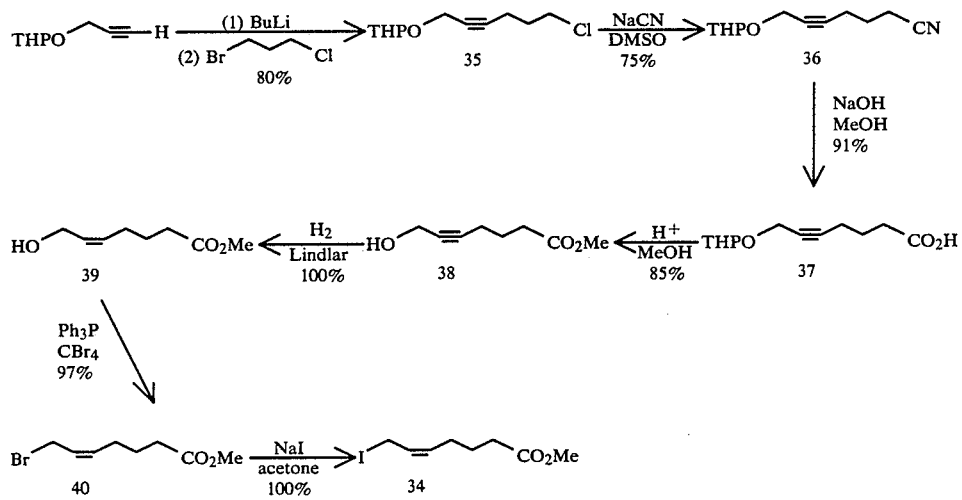

Catalytic acid in methanol concomitantly esterified the acid and deprotected the propargyl alcohol to give 38. This alkyne was contaminated with ca. 10% of allene 41 which could be separated with

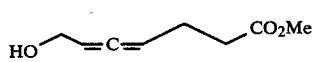

difficulty by flash chromatography. This byproduct arose from the previous step and could probably be eliminated by using alternate reaction conditions to accomplish this conversion (37→38).

Initially, the catalytic semihydrogenation of 38 was carried out using 5% palladium on barium sulfate in the presence of a catalyst poison, quinoline. The progress of the reaction was carefully monitored by TLC, but a 20–30% yield of the trans-alkene was always produced. The problem of stereomutation of cis-alkene on a palladium catalyst in the presence of hydrogen has been studied by Raphael (Dobson, N. A., et al., Tetrahedron 16, 16 (1961)). He found that the semihydrogenation of 4-octyne over 10% palladium on barium sulfate gave a 40% yield of the trans-alkene, while the Lindlar's catalyst (palladium on calcium carbonate, poisoned with lead) only a 4% yield of the trans-alkene was obtained. Use of the Lindlar catalyst dramatically reduced the amount of trans-alkene produced. Since the isomerization of cis- to trans-alkene occurs after all the alkyne has been reduced, the reaction must be carefully monitored by TLC. The rate of the reaction could be controlled by running it in a hexane/EtOAc mixture (2:1) at 0° C. Under these conditions, the reaction was completed in ca. 2-3 h. Reduction in this manner produced, at most, a 5% yield of the trans-alkene. Alcohol 39 was converted to bromide 40 in one of two ways: either with phosphorus tribromide and pyridine in ether or with carbon tetrabromide and triphenylphosphine in dichloromethane. The latter method was found to give the highest yields, 97% compared to 81%.

Bromide 40 was converted to iodide 34 immediately prior to use with sodium iodide in acetone and was used without purification. It is very important that the reaction time be limited to under ten minutes, since longer reaction times lead to appreciable amounts of the trans-alkene (Donaldson, R. E., et al. J. Am. Chem. Soc. 103, 2108 (1981)—See footnote).

Two other potential alkylating agents were also synthesized from alcohol 38. Iodide 42, required for the synthesis of 5,6-didehydro-PGE$_2$, was prepared from 38 in the same manner as described above (eq 21). The saturated iodide 44, required for the synthesis of PGE$_1$, was synthesized from 38 through a two-step reduction (Scheme 38).

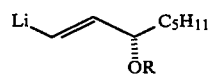

46

1-Octyn-3-ol was protected as the trimethylsilyl ether 47 and as the t-butyldimethylsilyl ether 48. Irradiation (GE 275 W sunlamp) of 47 or 48 with exactly one equivalent of tributyltin hydride[112] in the absence of solvent produced a mixture consisting of ca. 85% of the desired (E)-vinylstannanes 49 or 50 and 15% of a mixture thought to consist of the corresponding (Z)-vinylstannanes.

Scheme 39

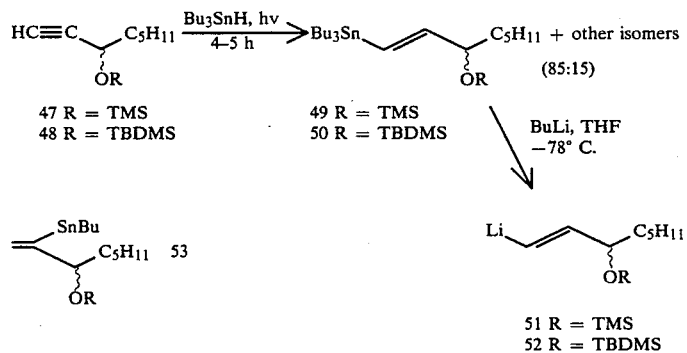

and a vinylstannane 53 resulting from addition of tin hydride with the opposite regiochemistry (Scheme 39). These ratios could easily be calculated from the integration of the vinyl proton resonances in the $^1$H NMR spectra. The thermally initiated addition of tributyltin hydride to 1-octyn-3-ol and its triethylsilyl ether have reportedly yielded only the (E)-vinylstannane. Other groups have reported the generation of mixtures and (E)- and (Z)-vinylstannane ω-chain analogues both by the thermally and the light initiated additions. The 85:15 ratio obtained in this reaction was independently verified in our laboratory. Longer reaction times or higher temperatures did not change this ratio significantly. These mixtures were transmetallated with n-BuLi in THF at −78° C. to give one vinyllithium product, 51 or 52. Under the reaction conditions the (Z)-vinylstannanes or 53 are not transmetallated appreciably. This selectivity has previously been noted. The presence of the undesired vinylstannanes, therefore, had no detrimental effect on the reaction. These vinylstannane mixtures were used as a mixture of isomers and were stored under argon at 0° C. without decomposition until needed.

This transmetallation reaction must be run in THF, as it proceeds only very slowly in diethyl ether. The reaction temperature must also be kept below −50° C., since at higher temperatures a 1,4 O→C silyl migration occurs to yield 54. Silyl ether (−)-48,

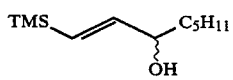

54 resolved via a steroidal ester and necessary for the efficient synthesis of optically pure prostaglandins, was converted to the vinylstannane mixture and transmetallated as described above.

α-SIDE-CHAIN VARIATIONS

Two PGE$_2$ analogues, (±)-5,6-didehydro-PGE$_2$ methyl ester (75) and its C-15 epimer 76, were synthesized using this same approach (Scheme 41). Addition of the stabilized organocuprate derived from racemic vinyllithium 52 to enone (±)-1 followed by alkylation with iodide 42 in the presence of HMPA provided, after chromatography, 77 as an inseparable mixture of two diastereomers in 40% yield. A large amount (ca. 40%) of the cis-alkylation product 79 was isolated, along with 18% of the unalkylated product 59. The cis product 79 was equilibrated to a 2:1 mixture of 77 and 79 in the usual manner to provide an additional 19% yield of 77 after chromatography (59% overall yield).

This alkylation was not successful. Alkylations with unactivated iodides in prostaglandin systems have previously given only low yields of alkylation.

Scheme 41

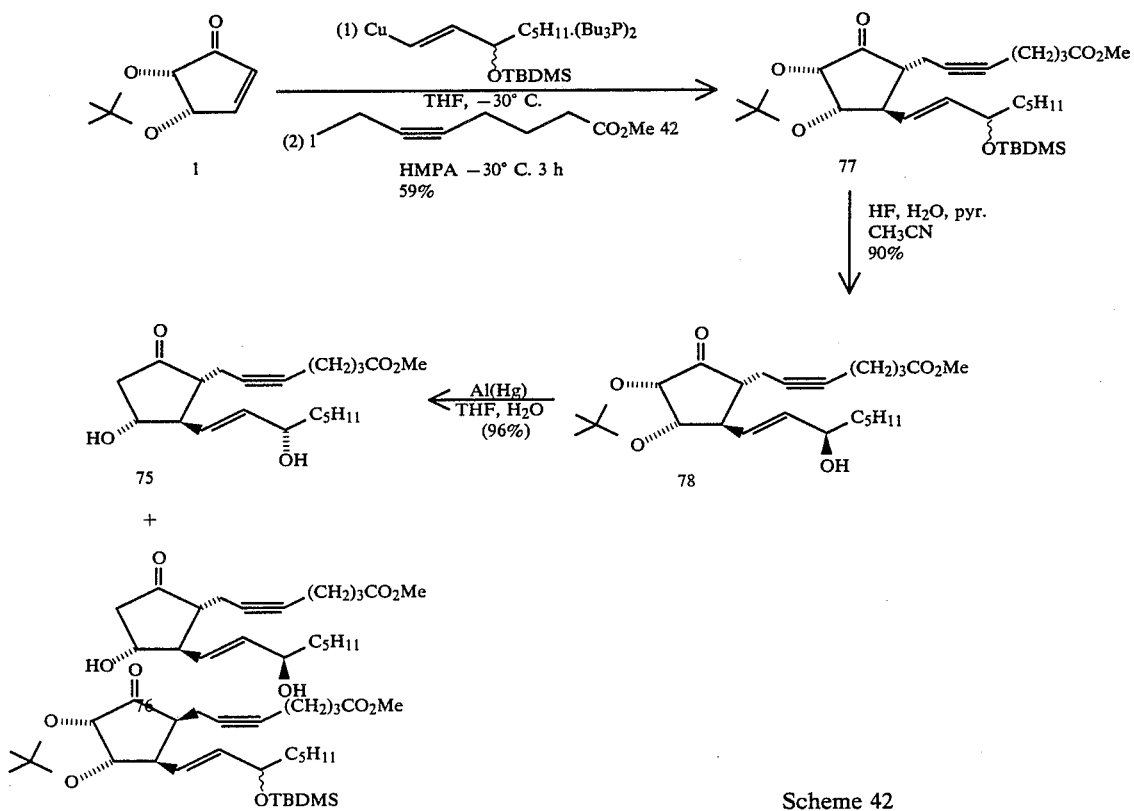

Silyl ether 77 was desilylated in acetonitrile containing 1% pyridine and 5% of a 50% aqueous solution of HF to provide, after flash chromatography, a 90% yield of 78 as a mixture of two diastereomers. These diastereomers were separable, but were carried on as a mixture. Only trace amounts of triol 80, from removal of the acetonide, were produced.

Reduction of 78 with aluminum amalgam proceeded much more rapidly and cleanly than the analogous PGE$_2$ case. Addition of three portions of Al(Hg) over 25 h to an aqueous THF solution of 78 produced an easily separable ($\alpha=1.53$) mixture of diastereomers 75 and 76. The synthesis of 75 had been previously described. Noyori has converted the bis-t-butyldimethylsilyl-protected 75 to PGE$_2$ methyl ester by catalytic semihydrogenation and to PGE$_1$ methyl ester by selective catalytic hydrogenation.

The alkylation of the lithium enolate of 59 with the saturated iodide 44 was attempted, the product of which would lead to a synthesis of PGE$_1$ (Scheme 42).

Scheme 42

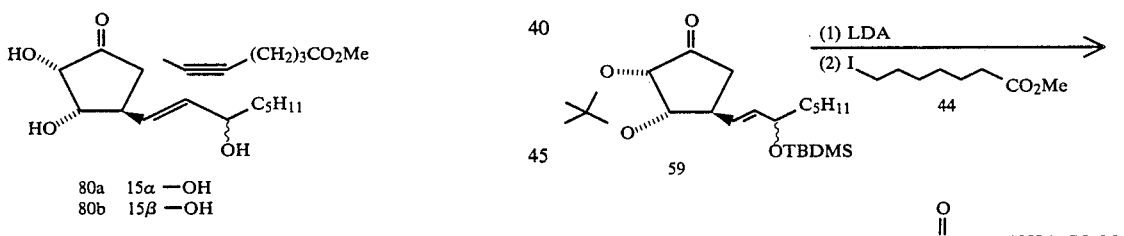

(+)-(3aS,5R,6R,6aS)-6-((3S)-tert-Butyldimethylsilyloxy-(1E)-octenyl)-5-(6-carbomethoxy-(2Z)-hexenyl)-2,2-dimethyl-3a,5,6,6a-tetrahydro-4H-cyclopenta-1,3-dioxol-4-one. ((+)-71).

A solution of (3S)-tert-butyldimethylsilyloxy-1-tributylstannyl-(1E)-octene (1.35 g, 2.54 mmol; prepared from (3S)-tert-butyldimethyl-silyloxy-1-octyne and tributyltin hydride as previously described) in dry THF (15 mL) at −78° C. was treated with n-BuLi (1.35 mL of a 1.6M solution, 2.16 mmol) and stirred at −78° C. for 20 min. A solution of CuI.Bu$_3$P (0.85 g, 2.16 mmol) and Bu$_3$P (0.54 mL, 2.16 mmol) in dry THF (5 mL) was added, and the reaction mixture was stirred at −78° C. for 30 min. A solution of enone (+)-1 (0.295 g, 1.19 mmol) in dry ether (5 mL) was added, and the mixture stirred at −78° C. for 10 min and at −30° C. for 1 h. HMPA (0.66 mL, 3.79 mmol) and a solution of iodide 34 (0.85 g, 3.17 mmol) in dry THF (5 mL) were added. After stirring at −30° C. for 3 h, the reaction mixture was poured into 20% aqueous ammonium sulfate (20 mL) and ether (20 mL). The ether layer was separated, washed with three 30-mL portions of water, dried over Na$_2$SO$_4$ concentrated by rotary evaporation. Flash chromatography, using 100:1 hexane/EtOAc slowly changing to 10:1 hexane/EtOAc, gave (+)-71 (0.475 g, 46%) as a colorless oil with the following characteristics: IR and $^1$H NMR identical to those of 64; $^{13}$C NMR (CDCl$_3$) δ 213.23, 173.82, 135.85, 130.97, 128.93, 126.72, 112.61, 80.74, 79.18, 72.82, 52.42, 51.33. 46.07, 38.16, 33.37, 31.69, 27.15, 26.90, 26.55, 25.80, 25.14, 24.83, 24.64, 22.51, 18.15, 13.88, −4.31, −4.81; $[\alpha]_D^{25}$ +7.55° (c 0.98, CHCl$_3$). Also isolated was the unalkylated product, (+)-(3aS,6S,6aS)-6-((3S)-tert-butyldimethyl-silyloxy-(1E)-octenyl)-2,2-dimethyl-3a,5,6,6a-tetrahydro-4H-cyclopenta-1,3-dioxol-4-one (+)-73, 0.192 g, 25%) as a colorless oil with $[\alpha]_D^{25}$ +102.2° (c 1.15, CHCl$_3$), and the cis-alkylated product 74 (0.120 g, 12%). Compound 74 was equilibrated to a mixture of 71 and 74 as previously described, and flash chromatography with 15:1 hexane/EtOAc to provide an additional 0.067 g (7%) of (+)-71 for a total yield of 53%.

(−)-(3aS,5R,6R,6aS)-5-(6-Carbomethoxy-(2Z)-hexenyl)-6-((3S)-hydroxy-(1E)-octenyl)-2,2-dimethyl-3a,5,6,6a-tetrahydro-4H-cyclopenta-1,3-dioxol-4-one ((−)-72).

A solution of (+)-71 (0.470 g, 0.876 mmol) in CH$_3$CN (30 mL) was cooled to 0° C. Pyridine (0.35 mL) was added, followed by 50% aqueous HF (1.75 mL). The reaction mixture was stirred at 0° C. for 10 min and at room temperature for 4.5 h. The mixture was poured into saturated aqueous NaHCO$_3$ (50 mL) and ether (50 mL). The ether layer was separated, washed with three 40-mL portions of water, dried over Na$_2$SO$_4$, and concentrated by rotary evaporation. Flash chromatography with 3:1 hexane/EtOAc as the eluent gave 0.064 g (14%) of starting silyl ether (+)-71 and 0.288 g (78%; 90% based on recovered (+)-71) of (−)-72 as a colorless oil: IR—same as that of 67: $^1$H NMR (CDCl$_3$ 5.66 (dd, J$_1$=15.5 Hz, J$_2$=7.0 Hz, H$_{14}$), 5.57 (dd, J$_1$=15.5 Hz, J$_2$=5.6 Hz, H$_{13}$), 5.37 (m, H$_5$ and H$_6$), 4.46 (q, J=6.7 Hz, H$_{10}$ and H$_{11}$), 4.06 (q, J=6.0 Hz, H$_{15}$), 3.63 (s, 3H), 2.62 (dt, J$_1$=7.3 Hz, J$_2$=2.6 Hz, H$_{12}$), 2.32 (m, 4H), 2.26 (t, J=7.4, 2H$_2$), 2.03 (dq, J$_1$=7.1 Hz, J$_2$=1.4 Hz, 2H$_4$), 1.63 (p, J=7.4 Hz, 2H$_3$), 1.57–1.13 (m, 8H), 1.38 (s, 3H), 1.29 (s, 3H), 0.84 (t, J=6.5 Hz, 3H); $^{13}$C NMR (CDCl$_3$) δ 212.49, 173.90, 135.44, 130.87, 129.95, 126.51, 112.76, 80.52, 78.90, 72.10, 52.47, 51.31, 46.67, 37.07, 33.24, 31.53, 26.78, 26.41, 26.35, 25.03, 24.94, 24.50, 22.39, 11.81; $[\alpha]_D^{25}$ −0.52° (c 2.29, CHCl$_3$). Anal. calcd for C$_{24}$H$_{38}$O$_6$: C, 68.22; H, 9.06. Found: C, 68.08; H, 9.05.

(−)-Prostaglandin E$_2$ Methyl Ester (−)-69)

To a solution of (−)-72 (0.280 g, 0.66 mmol) in 8:1 THF/water (25 mL) was added Al(Hg) (from 0.18 g, 0.0066 g-atoms of granular aluminum). Additional equal portions of Al(Hg) were added after 10 h, 17 h, and 23 h. After stirring an additional 15 h, the reaction mixture was filtered, and the filtrate poured into ether (20 mL) and water (20 mL). The ether layer was separated, dried over Na$_2$SO$_4$, and concentrated by rotary evaporation. Flash chromatography, first with 3:1 hexane/EtOAc, then with EtOAc, furnished (−)-72 (0.025 g, 9%) and (−)-PGE$_2$ methyl ester (0.216 g, 89%; 98% based on recovered (−)-72): $[\alpha]_D^{20}$ −71.8° (c 1.25, MeOH) [Lit. $[\alpha]_D^{20}$ −71.7° (c 1.04, MeOH)]. IR, $^1$H NMR, and $^{13}$C NMR data were in agreement with literature values and are described above for (±)-PGE$_2$ methyl ester.

Aluminum Amalgam Reduction of 78 5,6-Didehydroprostaglandin E$_2$ Methyl Ester (75) and 5,6-Dihydro-15-epiprostaglandin E$_2$ Methyl Ester (76).

Ketone 78 (18 mg, 0.043 mmol) was submitted to the usual Al(Hg) reduction conditions described above. After a total of 26 h, the reaction mixture was worked up to give a mixture of diols 75 and 76 (15 mg, 96%): R$_f$=0.19 and 0.29 (2:1 EtOAc/hexane), respectively; $^{124}$ $^1$H NMR (CDCl$_3$) δ 5.78 (2dd, J$_1$=15.3 Hz, J$_2$=6.6 Hz and 5.9 Hz, 1H), 5.64 (2dd, J$_1$=15.3 Hz, J$_2$=8.3 Hz, 1H), 4.17 (m, H$_{11}$ and H$_{15}$), 3.72 (s, 3H), 2.81 (dd, J$_1$=18 Hz, J$_2$=7 Hz, 1H), 2.73 (m, 2H), 2.44 (t, J=7 Hz, 2H), 2.40–2.03 (m, 7H), 1.83 (p, J=7 Hz, 2H), 1.67–1.23 (m, 8H), 0.91 (t, 3H); high resolution mass spectrum (CI conditions), m/e 365.2332 (calcd for C$_{21}$H$_{33}$O$_5$ (M+H), 365.2328). The product mixture was not further purified.

6-(3-tert-Butyldimethylsilyloxy-(1E)-octenyl)-5-(6-carbomethoxy-2-hexynyl)-2,2-dimethyl-3aβ,5β,6α,6aβ-tetrahydro-4H-cyclopenta-1,3-dioxol-4-one (77)

To the vinyllithium reagent 52 (from the transmetallation of the vinyltin reagent 50 (0.52 g, 0.98 mmol)) in dry THF (4 mL) at −78° C. was added a solution of CuI.Bu$_3$P (0.31 g, 0.78 mmol) and Bu$_3$P (0.19 mL, 0.78 mmol) in dry THF (2 mL). After stirring at −78° C. for 30 min, a solution of enone (±)-1 (0.11 g, 0.71 mmol) in dry Et$_2$O (2 mL) was added. The reaction mixture was stirred at −78° C. for 10 min and at −30/° C. for 1 h. HMPA (0.25 mL, 1.43 mmol) and a solution of propargyl iodide 42 (0.30 g, 1.13 mmol) in dry THF (1 mL) were added, and the mixture was stirred at −30° C. for 3 h. The usual workup, followed by flash chromatography with 15:1 hexane/EtOAc, gave the unalkylated product 59 (0.087 g, 18%), the cis-alkylated product 79 (0.150 1 g, 39%), and the desired 77 (0.153 g, 40%; an inseparable mixture of two diastereomers) as a colorless oil: IR (neat) 2960 (s), 2940 (s), 2860, 1760 (s), 1745 (s), 1465, 1440, 1375, 1250, 1215, 1160, 1070, 970, 835, 775 cm$^{-1}$; $^1$H NMR (CDCl$_3$) δ 5.68 (m, J=15 Hz, H$_{13}$ and H$_{14}$), 4.57 (m, H$_{10}$ and H$_{11}$), 4.16 (m, H$_{15}$), 3.71 (s, 3H), 2.99 (m, H$_{12}$), 2.48 (m, 3H), 2.44 (t, J=7.4 Hz, 2H), 2.22 (tt, J$_1$=6.9 Hz, J$_2$=2.0 Hz, 2H), 1.81 (p, J=7.2 Hz, 2H), 1.49–1.23 (m, 8H), 1.45 (s, 3H), 1.39 (s, 3H), 0.93 (m, 12H), 0.06 (2s, 6H); $^{13}$C NMR (CDCl$_3$) δ 211.56*, 173.57, 136.34*, 128.44*, 112.88*, 80.69, 80.60, 79.19, 77.07, 72.88, 51.72, 51.43, 46.18*, 38.21, 32.82, 31.74, 27.01, 25.85, 25.40, 24.92, 24.81, 24.06, 22.55, 18.38, 18.21*, 13.95, −4.24, −4.75; high resolution mass spectrum m/e 534.3372 (calcd for $C_{30}H_{50}O_6Si$, 534.3376). The cis-alkylation product 79 was equilibrated as described above and flash chromatographed (15:1 hexane/EtOAc) to give 0.072 g (19%) of 77, for an overall yield of 0.225 g (59%) of 77.

The Desilylation of 77

5-(6-Carbomethoxy-2-hexynyl)-6-(3-hydroxy-(1E)-octenyl)-2,2-dimethyl-3aβ,5β,6α,6aβ-tetrahydro-4H-cyclopenta-1,3-dioxol-4-one (78).

Silyl ether 77 (0.090 g, 0.168 mmol) was stirred in $CH_3CN$ (3 mL) and cooled to 0° C. Pyridine (0.10 mL) was added, followed by 50% aqueous HF (0.30 mL). The reaction mixture was warmed to room temperature and stirred for 3 h. The mixture was worked up in the same manner as described above to give crude 78 (0.068 g, 96%). Flash chromatography using 2:1 hexane/EtOAc furnished 78 (a mixture of two diastereomers) as a colorless oil: $^1H$ NMR ($CDCl_3$) δ 5.77 (m, J=15 Hz, 2H), 4.55 (m, $H_{10}$ and $H_{11}$), 4.18 (m, $H_{15}$), 3.72 (s, 3H), 2.97 (m, J=3 Hz, $H_{12}$), 2.51 (m, 3H), 2.43 (t, J=7.4 Hz, 2H), 2.22 (tt, $J_1$=6.9 Hz, $J_2$=2.3 Hz, 2H), 1.80 (p, J=7.2 Hz, 2H), 1.73–1.18 (m, 9H), 1.44 (s, 3H), 1.37 (s, 3H), 0.91 (t, 3H).

trans-1-Tributylstannyl-3-trimethylsilyloxy-1-octene (49)

Under an argon atmosphere, 3-trimethylsilyloxy-1-octyne (47, 2.00 g, 10.08 mmol) and tributyltin hydride (2.70 mL, 10.18 mmol) were irradiated with a 275 W GE sunlamp, without solvent, for 4 h to produce 49: $^1H$ NMR ($CDCl_3$) δ 6.04 (d, J=18.9 Hz, 1H), 5.93 (dd, $J_1$=18.9 Hz, $J_2$=5.4 Hz, 1H), 4.04 (q, $J_1$=6.5 Hz, $J_2$=5.6 Hz, 1H), 1.52, 1.34 (2m, 26H), 0.91 (m, 12H), 0.11 (s, 9H). $^1H$ NMR analysis revealed that 49 was only ca. 85% pure. Other isomers, presumed to be the cis-vinyl-stannane and the regioisomeric vinylstannane, could be clearly seen in the vinyl region of the NMR spectrum. The production of these impurities in this reaction has been previously described.

trans-3-tert-Butyldimethylsilyloxy-1-tributylstannyl-1-octene (50)

Irradiation of 3-(tert-butyldimethylsilyloxy)-1-octyne (48, 2.05 g, 8.53 mmol) and tributyltin hydride (2.30 mL, 8.53 mmol) under the conditions described above yielded 50: $^1H$ NMR ($CDCl_3$) δ 6.04 (d, J=19.0 Hz, 1H), 5.93 (dd, $J_1$=19.0 Hz, $J_2$=5.2 Hz, 1H), 4.04 (dd, $J_1$=6.1 Hz, $J_2$=5.6 Hz, 1H), 1.52, 1.34 (2m, 26H), 0.94 (m, 21H), 0.07 (s, 3H), 0.05 (s, 3H). $^1H$ NMR analysis revealed that 50 was only 85% pure and presumably contained the same isomeric impurities as did 49.

Addition of trans-3-Trimethylsilyloxy-1-octenylcuprates to (±)-1; 6-(3-Hydroxy-(1E)-octenyl)-2,2-dimethyl-3aβ,5,6α,-6aβ-tetrahydro-4H-cyclopenta-1,3-dioxol-4-one (58)

A. Mixed Homocuprate ($C_3H_7C≡CCuR$)Li. A solution of 1-pentyne (0.07 mL, 0.70 mmol) in dry $Et_2O$ (2 mL) was treated with n-BuLi (0.44 mL of a 1.6M solution, 0.70 mmol) at 0° C. and stirred for 10 min. A solution of copper (I) iodide/tri-n-butylphosphine complex ($CuI·Bu_3P$, 0.27 g, 0.69 mmol) in dry THF (1 mL) was added. The yellow, homogeneous solution was warmed to room temperature and stirred for 10 min. Concurrently, trans-1-lithio-3-trimethylsilyloxy-1-octene (51) was prepared by addition of n-BuLi (0.41 mL of a 1.6M solution, 0.65 mmol) to a solution of the vinyltin 49 (0.38 g, 0.77 mmol) in dry THF (3 mL) at −78° C. and stirring for 20 min at −78° C. (Although reagent 49 was contaminated with 15% of other isomers, only the desired isomer was appreciably transmetallated under the reaction conditions.) To this solution was added the initially described organocopper solution, and the yellow heterogeneous mixture was stirred at −78° C. for 45 min. A solution of enone(±)-1 (0.090 g, 0.58 mmol) in dry $Et_2O$ (2 mL) was added, and the mixture stirred at −78° C. for 30 min and at −30° C. for 1 h. The reaction mixture was quenched with 20% aqueous ammonium sulfate (5 mL) and poured into $Et_2O$ (10 mL) and water (5 mL). Extraction with two 15-mL portions of $Et_2O$, drying of the combined ether extracts over $Na_2SO_4$, and concentration by rotary evaporation afforded the crude, trimethylsilyl-protected product 57, which could be purified by flash chromatography (50:1 hexane/EtOAc) to yield 57 as a mixture of two diastereomers: IR (neat) 2990(w), 2960 (s), 2935 (s), 2860, 1760 (s), 1460 (w), 1382, 1373, 1250, 1210, 1155, 1060 (s), 970, 840 (s), $cm^{-1}$; $^1H$ NMR ($CDCl_3$) δ 5.54 (m, $J_1$=15.6 Hz, $J_2$=5.1 Hz, 2H), 4.61 (d, J=5.3 Hz, $H_{10}$), 4.19 (dd, $J_1$=5.3 Hz, $J_2$=0.6 Hz, $H_{11}$), 4.04 (m, $H_{15}$), 3.11 (m, $H_{12}$), 2.85 (dddd, $J_1$=18.2 Hz, $J_2$=8.5 Hz, $J_3$=2.6 Hz, $J_4$=0.7 Hz, $H_8$), 2.24 (br d, J=18.2 Hz, $H_8$), 1.52–1.14 (m, 8H), 1.46 (s, 3H), 1.36 (s, 3H), 0.89 (t, J=7.0 Hz, 3H), 0.10 (s, 9H); $^{13}C$ NMR ($CDCl_3$) δ 213.19, 135.70, 128.11, 112.41. 81.79*, 77.93, 72.73*, 39.16, 38.61*, 38.00, 31.65, 26.81, 25.04, 24.89, 22.50, 13.92, 0.22 (*denotes a doublet due to the presence of two diastereomers). Generally, it was found to be more efficient to deprotect the crude 57 prior to purification. The crude product 57 was stirred in MeOH (10 mL) at 0° C. and a catalytic amount of $K_2CO_3$ was added. The reaction mixture was stirred at 0° C. for 15 min and at room temperature for 1.5 h. The mixture was concentrated by rotary evaporation, dissolved in diethyl ether (20 mL), washed twice with water (20 mL), dried over $Na_2SO_4$, and concentrated by rotary evaporation to give, after flash chromatography with 3:1 hexane/EtOAc, 58 (0.078 g, 48%) (, a colorless oil as a mixture of two diastereomers: IR (neat) 3470 (br), 2990, 2930 (s), 2860, 1757 (s), 1455, 1405, 1380, 1370, 1210, 1150, 1060, 970, 850, 805 (w), $cm^{-1}$; $^1H$ NMR ($CDCl_3$) δ 5.62 (dd, $J_1$=15.8 Hz, $J_2$=6.2 Hz, $H_{14}$), 5.53 (dd, $J_1$=15.8 Hz, $J_2$=5.6 Hz, $H_{13}$), 4.60 (d, J=5.1 Hz, $H_{10}$), 4.18 (t, J=5.1 Hz, $H_{11}$), 4.04 (q, J=5.8 Hz, $H_{15}$), 3.08 (t, J=7.2 Hz, $H_{12}$), 2.82 (dd, $J_1$=18.2 Hz, $J_2$=8.5 Hz, $H_8$), 2.22 (br d, J=18.2 Hz, $H_8$), 1.93 (br, —OH), 1.58–1.13 (m, 8H), 1.41 (s, 3H), 1.32 (s, 3H), 0.86 (t, J=7.0 Hz, 3H); $^{13}C$ NMR ($CDCl_3$) δ 213.06, 135.11, 129.22, 112.39, 81.60, 77.81, 72.14, 39.15*, 38.67, 37.18, 31.55, 26.71, 24.90, 24.80, 22.43, 13.87; high resolution mass spectrum, m/e 282.1826 (calcd for $C_{16}H_{26}O_4$, 282.1831). Anal. calcd for $C_{16}H_{26}O_4$: C, 68.05; H, 9.28. Found: C, 68.39; H, 9.31.

B. Mixed Homocuprate [$Ph_2P(S)CH_2CuR$]Li.[118] A solution of methyldiphenylphosphine sulfide (0.151 g, 0.65 mmol) in dry THF (2 mL) at 0° C. was treated with n-BuLi (0.41 mL of a 1.6M solution, 0.65 mmol) and stirred for 15 min. This solution was transferred to a suspension of CuI (0.124 g, 0.65 mmol) in dry THF (4 mL) at −78° C. The reaction mixture was warmed to 0° C., stirred at 0° C. for 15 min, and cooled to −78° C. To the brown, homogeneous solution was added the vinyllithium reagent 51 (from the transmetallation of the vinyltin reagent 49 (0.38 g, 0.77 mmol)) in dry THF (2 mL). The brown mixture was stirred at −78° C. for 30 min and a solution of enone (±)-1 (0.09 g, 0.58 mmol) in dry Et$_2$O (2 mL) was added. After stirring at −78° C. for 30 min and at −30° C. for 1 h, the reaction mixture was quenched and worked up in the usual manner to afford crude 57. This was immediately deprotected with catalytic K$_2$CO$_3$ in MeOH (10 mL) and flash chromatographed with 3:1 hexane/EtOAc to give 58 (0.094 g, 57%) with spectral characteristics identical to those previously described.

C. Mixed Homocuprate [Ph$_2$P(S)CH$_2$CuR]Li in the presence of Bu$_3$P. A solution of methyldiphenylphosphine sulfide (0.151 g, 0.65 mmol) in dry THF (2 mL) at 0° C. was treated with n-BuLi (0.41 mL of a 1.6M solution, 0.65 mmol) and stirred for 15 min. This solution was added to a solution of CuI.Bu$_3$P (0.255 g, 0.65 mmol) in dry THF (4 mL) at −78° C. The reaction mixture was warmed to 0° C., stirred at 0° C. for 15 min, and cooled to −78° C. To the light brown, homogeneous solution was added the vinyllithium reagent 51 (from the transmetallation of the vinyltin reagent 49 (0.38 g, 0.77 mmol)) in dry THF (2 mL). The brown mixture was stirred at −78° C. for 30 min and a solution of enone (±)-1 (0.09 g, 0.58 mmol) in dry Et$_2$O (2 mL) was added. After stirring at −78° C. for 30 min and at −30° C. for 1 h, the reaction mixture was quenched and worked up in the usual manner. Deprotection, followed by flash chromatography as described above, yielded 58 (0.110 g, 67%).

D. Mixed Homocuprate [CH$_3$S(O)CH$_2$CuR]Li. A solution of dry DMSO (0.17 mL, 2.40 mmol) in dry THF (5 mL) at 0° C. was treated with 1 equiv n-BuLi and stirred for 15 min at 0° C. This solution was added to a solution of CuI.Bu$_3$P (0.943 g, 2.40 mmol) in dry THF (10 mL) at 0° C. The light-yellow, heterogeneous solution was stirred at 0° C. for 20 min and cooled to −78° C. To this solution was added the vinyllithium reagent 51 (from the transmetallation of the vinyltin reagent 49 (1.38 g, 2.82 mmol)) in dry THF (5 mL). The orange, heterogeneous solution was stirred at −78° C. for 30 min. A solution of enone (±)-1 (0.310 g, 2.01 mmol) in dry Et$_2$O (5 mL) was added, and the reaction was stirred at −78° C. for 15 min and at −30° C. for 1 h. Workup, deprotection, and flash chromatography as previously described furnished 58 (0.44 g, 78%).

E. Stabilized Organocopper Reagent RCu.Bu$_3$P. To the vinyllithium reagent 51 (from the transmetallation of the vinyltin reagent 49 (1.51 g, 3.07 mmol)) in dry THF (15 mL) at −78° C. was added a solution of CuI.Bu$_3$P (1.02 g, 2.60 mmol) and Bu$_3$P (0.65 mL, 2.60 mmol) in dry THF (10 mL). The yellow, homogeneous solution was stirred at −78° C. for 30 min, and a solution of enone (±)-1 (0.335 g, 2.17 mmol) in dry Et$_2$O (5 mL) was added. After stirring at −78° C. for 15 min and at −30° C. for 1 h, the reaction mixture was worked up, deprotected, and flash chromatographed as previously described to give 58 (0.485 g, 79%).

6-(3-tert-Butyltrimethylsilyloxy-(1E)-octenyl-2,2-dimethyl-3aβ,5,6α,6aβ-tetrahydro-4H-cyclopenta-1,3-dioxol-4-one (59)

Method A. Addition of Stabilized Organocopper Reagent. A solution of vinyltin reagent 50 (0.80 g, 1.50 mmol) in dry THF (5 mL) at −78° C. was transmetallated with n-BuLi as described previously. A solution of CuI.Bu$_3$P (0.47 g, 1.20 mmol) and Bu$_3$P (0.30 mL, 1.20 mmol) in dry THF (3 mL) was added, and the reaction mixture was stirred at −78° C. for 30 min. After addition of a solution of enone (±)-1 (0.154 mmol, 1.00 mmol) in dry Et$_2$O (2 mL), the reaction mixture was stirred at −78° C. for 10 min and at −30° C. for 1 h. The usual workup procedure followed by flash chromatography using 50:1 hexane/EtOAc yielded 59 (0.370 g, 93%), a colorless oil, as an inseparable mixture of two diastereomers: $^1$H NMR (CDCl$_3$) δ 5.56 (ddd, J$_1$=15.7 Hz, J$_2$=5.3 Hz, J$_3$=2.2 Hz, H$_{14}$), 5.49 (ddd, J$_1$=15.7 Hz, J$_2$=4.8 Hz, J$_3$=2.0 Hz, H$_{13}$), 4.61 (d, J=5.2 Hz, H$_{10}$), 4.16 (d, J=5.2 Hz, H$_{11}$), 4.07 (m, H$_{15}$), 3.10 (m, H$_{12}$), 2.83 (ddd, J$_1$=18.1 Hz, J$_2$=8.4 Hz, J$_3$=0.8 Hz, H$_8$), 2.22 (dd, J$_1$=18.1 Hz, J$_2$=0.8 Hz, H$_8$), 1.51–1.13 (m, 8H), 1.44 (s, 3H), 1.35 (s, 3H), 0.87 (2s, t, J=6.8 Hz, 12H), 0.02–0.01 (2s, 6H); $^{13}$C NMR (CDCl$_3$) δ 213.11*, 135.74, 127.88, 112.31, 81.69*, 77.82, 72.72, 38.99, 38,39*, 38.07, 31.65, 26.77*, 25.76*, 24.87, 24.77, 22.48, 18.11, 13.91*, −4.40, −4.86. Anal. calcd for C$_{22}$H$_{40}$O$_4$Si: C, 66.62; H, 10.16, Found: C, 66.62; H, 10.05.

Method B. Addition of Mixed Homocuprate [CH$_3$S(O)CH$_2$CuR]Li. A solution of dry DMSO (0.057 mL, 0.80 mmol) in dry THF (3 mL) at 0° C. was treated with 1 equiv of n-BuLi and stirred for 15 min. The white slurry was added to a solution of CuI.Bu$_3$P (0.314 g, 0.80 mmol) in dry THF (5 mL) at −78° C. The reaction mixture was warmed to 0° C., stirred at 0° C. for 20 min, and cooled to −78° C. To this solution was added the vinyllithium reagent 52 (from the transmetallation of the vinyltin reagent 50 (0.53 g, 1.00 mmol)) in dry THF (3 mL). After stirring at −78° C. for 20 min, a solution of (±)-1 (0.11 g, 0.71 mmol) in dry Et$_2$O (3 mL) was added. The mixture was stirred at −78° C. for 15 min and at −30° C. for 1 h. The reaction mixture was worked up in the usual manner and flash chromatographed using 50:1 hexane/EtOAc to give 59 (0.25 g, 89%) with spectral characteristics identical to those described above.

2-(6-Chloro-2-octynyloxy)tetrahydropyran (35)

A solution of 2-propynyloxytetrahydropyran (28.00 g, 0.200 mol) in dry THF (500 mL) at 0° C. was treated with n-BuLi (125 mL of a 1.6M solution, 0.200 mol) and stirred at 0° C. for 15 min. A solution of 1-bromo-3-chloropropane (31.50 g, 0.200 mol) in dry THF (50 mL) was added. The reaction mixture was warmed to room temperature and then refluxed for 20.5 h. The mixture was cooled, poured into a separatory funnel, and washed with two 200-mL portions of water. The organic layer was dried over Na$_2$SO$_4$ and concentrated by rotary evaporation to yield, after distillation (110°–112° C./0.4 torr), 35 as a colorless oil (38.80 g, 78%): IR (neat) 2950 (s), 2875, 2290 (w), 2230 (w), 1445, 1350, 1205, 1130 (s), 1120 (s), 1080, 1055, 1025 (s), 900, 870, 815 cm$^{-1}$; $^1$H NMR (CDCl$_3$) δ 4.79 (t, J=3.1 Hz, 1H), 4.25 (tq, J$_1$=15.3 Hz, J$_2$=2.2 Hz, 2H), 3.84 (dq, J$_1$=8.5 Hz, J$_2$=3.1 Hz, 1H), 3.66 (t, J=6.4 Hz, 2H), 3.53 (m, 1H), 2.43 (tt, J$_1$=6.8 Hz, J$_2$=2.1 Hz, 2H), 1.98 (p, J=6.6 Hz, 2H), 1.92–1.48 (m, 6H).

2-(6-Cyano-2-octynyloxy)tetrahydropyran (36)

A solution of chloride 35 (20.0 g, 92.3 mmol) in dry DMSO (75 mL) was added to a solution of NaCN (6.0 g, 122.0 mmol) in dry DMSO (100 mL). The reaction mixture was stirred at 50°–60° C. for 65 h. The dark brown mixture was cooled, poured into water (200 mL), and extracted with five 100-mL portions of CH$_2$Cl$_2$. The combined organic extracts were washed with water (3×150 mL), dried over Na$_2$SO$_4$, and concentrated by rotary evaporation. The black oil was dissolved in Et$_2$O (200 mL) and filtered through a pad of silica gel (60-200 mesh, Baker Chemical Co.) to yield 36 as a yellow oil (14.3 g, 75%): IR (neat) 2940 (s), 2870, 2280 (w), 2250, 1440, 1345, 1200, 1130, 1115 (s), 1075, 1020 (s), 900, 865, 810 cm$^{-1}$; $^1$H NMR (CDCl$_3$)δ 4.80 (m, 1H), 4.23 (t, J=2 Hz, 2H), 3.66 (m, 2H), (m, 4H), 1.67 (m, 8H). Nitrile 36 was used without further purification.

7-(Tetrahydropyranyl-2-oxy)-5-heptynoic Acid (37)

To a solution of nitrile 36 (12.40 g, 60.0 mmol) in MeOH (175 mL) was added 10% aqueous NaOH (100 mL). The mixture was refluxed for 19.5 h, cooled, and concentrated to a volume of 150 mL on a rotary evaporator. The basic solution was acidified to congo red with 2M aqueous HCl (ca. 130 mL), followed by extraction with five 100-mL portions of Et$_2$O. The combined organic extracts were dried over Na$_2$SO$_4$ and filtered through a pad of silica gel (60-200 mesh, Baker Chemical Co.). Concentration by rotary evaporation afforded 37 as a yellow oil (12.30 g, 91%): IR (neat) 3680-2340 (br), 2950 (s), 2290 (w), 2230 (w), 1740 (s), 1715 (s), 1440, 1350, 1200, 1130 (s), 1115 (s), 1075, 1055, 1020 (s), 900, 865, 810 cm$^{-1}$; $^1$H NMR (CDCl$_3$) δ 8.82 (br, 1H), 4.73 (m, 1H), 4.16 (m, 2H), 3.50 (m, 2H), 2.36 (m, 4H), 1.62 (m, 8H). Acid 37 was used without further purification.

Methyl 7-Hydroxy-5-heptynoate (38)

A solution of acid 37 (12.20 g, 54.0 mmol) and p-toluenesulfonic acid hydrate (200 mg) in MeOH (150 mL) was refluxed for 36 h. The reaction mixture was cooled and concentrated by rotary evaporation. The residue was dissolved in Et$_2$O (200 mL), washed with saturated, aqueous NaHCO$_3$ (100 mL) and water (100 mL), dried over Na$_2$SO$_4$, and concentrated by rotary evaporation. Distillation (103°-105° C./0.8 torr) furnished 38 as a colorless oil (7.2 g, 85%): R$_f$: −0.68 (2:1 EtOAc/hexane); IR (neat) 3440 (br), 2950 (s), 2870, 2280 (w), 2220 (w), 1740 (s), 1440 (s), 1370, 1225, 1160, 1010 cm$^{-1}$; $^1$H NMR (CDCl$_3$) δ 4.24 (m, 2H), 3.68 (s, 3H), 2.44 (t, J=7.4 Hz, 2H), 2.29 (tt, J$_1$=6.9 Hz, J$_2$=2.1 Hz, 2H), 1.83 (p, J=7.1 Hz, 2H); $^{13}$C NMR (CDCl$_3$) δ 173.65, 84.72, 79.34, 51.50, 51.02, 32.72, 23.61, 18.08. anal. calcd for C$_8$H$_{12}$O$_3$: C, 61.52; H, 7.74. Found: C, 61.37; H, 7.75. Alkyne 38 was contaminated with ca. 10% of a compound presumed to be methyl 7-hydroxy-4,5-heptadienoate (41). Allene 41 could be separated from the desired alkyne 38 by a tedious flash chromatography using 4:1 hexane/EtOAc. Allene 41 [R$_f$=0.63 (2:1 EtOAc/hexane)] was characterized by multiplets at δ 5.38 and 4.09 in the $^1$H NMR spectrum and by singlets at δ 92.81 and 91.34 in the $^{13}$C NMR spectrum.

Methyl cis-7-Hydroxy-5-heptenoate (39)

Lindlar catalyst (palladium on calcium carbonate, poisoned with lead; 60 mg) was added to a solution of alkyne 38 (1.26 g, 8.07 mmol) in 2:1 hexane/EtOAc at 0° C. Hydrogen was bubbled through the reaction mixture until TLC analysis indicated the disappearance of 38 (2-3 h). The mixture was filtered and concentrated to yield 39 was a colorless liquid (1.277 g, 100%): IR (neat) 3410 (br), 3015 (w), 2940 (s), 2860, 1740 (s), 1435,, 1365, 1245, 1205, 1155, 1025, 1000 cm$^{-1}$; $^1$H NMR (CDCl$_3$) δ 5.66 (ddt, J$_1$=10.9 Hz, J$_2$-6.8 Hz, J$_3$=1.4 Hz, 1H), 5.44 (dtt, J$_1$=10.9 Hz, J$_2$=7.5 Hz, J$_3$=1.3 Hz, 1H), 4.15 (dd, J$_1$=6.7 Hz, J$_2$=1.1 Hz, 2H), 3.66 (s, 3H), 2.32 (t, J=7.3 Hz, 2H), 2.12 (dq, J$_1$=7.5 Hz, J$_2$=1.1 Hz, 2H), 1.99 (br, 1H), 1.71 (p, J=7.3 Hz, 2H9. A minor amount (ca. 3%) of methyl trans-7-hydroxy-5-heptenoate could be seen in the $_1$H NMR spectrum at δ 4.09. The longer the reaction proceeded beyond completion, the greater the amount of this product was produced.

Methyl cis-7-Bromo-5-heptenoate (40)

To a solution of alcohol 39 (1.48 g, 9.36 mmol) and carbon tetrabromide (3.40 g, 10.25 mmol) in dry CH$_2$Cl$_2$ (50 mL) was added triphenylphosphine (2.70 g, 10.30 mmol) in portions. The reaction mixture was stirred for 40 min and MeOH (1 mL) was added. Concentration on a rotary evaporator, followed by flash chromatography using 50:1 hexane/EtOAc as eluent, gave 40 as a colorless oil (1.98 g, 96%): IR (neat) 3020 (w), 2945, 2860 (w), 1740 (s), 1435, 1370, 1200, 1165 cm$^{-1}$; $^1$H NMR (CDCl$_3$) δ 5.77 (m, J$_1$=10.5 Hz, J$_2$=8.3 Hz, J$_3$=1.4 Hz, 1H), 5.56 (m, J$_1$=10.6 Hz, J$_2$=7.5 Hz, 1H), 3.98 (d, J=8.1 Hz, 2H), 3.67 (s, 3H), 2.34 (t, J=7.4 Hz, 2H), 2.19 (dq, J$_1$=7.5 Hz, J$_2$=1.4 Hz, 2H), 1.74 (p. J=7.3 Hz, 2H); $^{13}$C NMR (CDCl$_3$) δ 173.55, 134.48, 126.26, 51.37, 33.06, 26.60, 26.01, 24.28. A minor amount (ca. 5%) of methyl trans-7-bromo-5-heptenoate could be seen in the $^1$H NMR spectrum at δ 3.93.

Methyl 7-Bromo-5-heptynoate (60)

A solution of alcohol 38 (1.95 g, 12.5 mmol) and pyridine (0.20 mL, 2.60 mmol) in dry Et$_2$O (15 mL) was cooled to 0° C. Phosphorus tribromide (0.60 mL, 6.4 mmol) was added dropwise, and the reaction mixture was stirred at 0° C. for 30 min and at room temperature for 1 h. The mixture was poured into water (10 mL) and the organic layer was washed with two 10-mL portions of water. Drying over Na$_2$SO$_4$ and concentration by rotary evaporation furnished, after flash chromatography using 20:1 hexane/EtOAc, 60 as a colorless oil (2.18 g, 80%): IR (neat) 3010 (w), 2950, 2300 (w), 2230, 1740 (s), 1435 (s), 1370, 1315, 1220 (s), 1160 (s), cm$^{-1}$; $^1$H NMR (CDCl$_3$) δ 3.89 (t, J=2.3 Hz, 2H), 3.65 (s, 3H), 2.40 (t, J=7.4 Hz, 2H), 2.29 (tt, J$_1$=6.9 Hz, J$_2$=2.3 Hz, 2H), 1.80 (p, J=7.1 Hz, 2H); $^{13}$C NMR (CDCl$_3$) δ 173.23, 86.56, 76.10, 51.42, 32.56, 23.40, 18.23, 15.18.

Methyl cis-7-Iodo-5-heptenoate (34)

To a solution of bromide 40 (0.29 g, 1.30 mmol) in dry acetone (10 mL) was added NaI (0.26 g, 1.70 mmol). The reaction mixture was stirred for 5 min, filtered, and poured into Et$_2$O (50 mL) and water (20 mL). The ether layer was separated, washed with three 20-mL portions of water, dried over Na$_2$SO$_4$, and concentrated by rotary evaporation to yield the iodide 34 (0.35 g, 100%). The iodide was used immediately without further purification. If the reaction mixture was stirred for longer than 5 min, isomerization of the cis- to the transallyl iodide began to take place.

It is intended that the foregoing examples be only illustrative of the process and compounds of the present invention. Since the specific examples involved the most complex reactants to produce the cyclopentanoids (I), it will be obvious to those skilled in the art that less complex intermediates will work as well. It is intended that the present invention be limited only by the hereinafter appended claims.

We claim:

1. The process for the preparation of a cyclopentanoid (I) which comprises:

(a) reacting in an organic solvent at a reduced temperature less than ambient temperatures a compound of the formula:

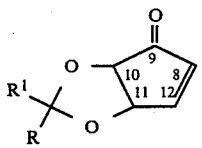

including stereoisomers wherein R and R' CO— provide a protecting group for the C-11 oxygen group and the C-10 methylene group and with a compound of the formula:

R$_\omega$Cu wherein R$_\omega$Cu is a copper complex soluble in the organic solvent wherein R$_\omega$ is selected from alkyl and alkenyl groups containing 4 to 12 carbon atoms to form an intermediate of the formula:

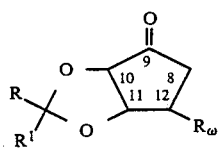 (II)

including stereoisomers;
(b) reacting II with R$_\alpha$X in an organic solvent wherein R$_\alpha$ is selected from alkenyl and alkynyl ester, ketone and amide groups containing 3 to 12 carbon atoms and X is a halogen selected from chloro- and iodo- and bromo-groups to form a compound of the formula:

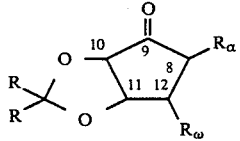 (III)

including stereoisomers;
(c) reacting (III) in an aqueous organic solvent mixture with a metallic reducing agent to produce a compound of the formula:

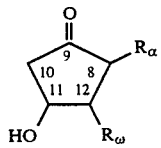 (I)

including stereoisomers as the prostanoid (I).
2. The process of claim 1 wherein —R$_2$CO$_2$R$_3$ is —CH$_2$—CH=CH—(CH$_2$)$_3$—CO$_2$CH$_3$.
3. The process for the preparation of a cyclopentanoid (I) which comprises:
(a) reacting in an organic solvent at a reduced temperature less than ambient temperatures a compound of the formula:

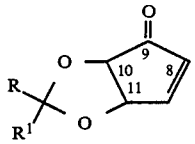

when R and R' CO— together provide a protecting group selected from lower alkyl, aralkyl and aryl carboxy groups which may be the same or different and stereoisomers thereof with a compound of the formula:

R$_\omega$Cu when R$_\omega$Cu is a copper complex soluble in the organic solvent wherein R$_\omega$ is selected from alkyl or alkenyl groups containing 4 to 12 carbon atoms to form an intermediate of the formula:

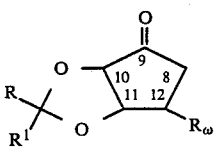 (II)

including stereoisomers;
(b) reacting II with R$_\alpha$X in an organic solvent wherein R$_\alpha$ is selected from alkenyl and alkynyl ester groups containing 3 to 12 carbon atoms and X is a halogen selected from chloro- and iodo- and bromo groups to form a compound of the formula:

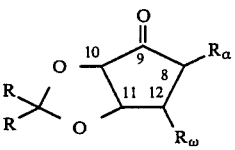 (III)

or including stereoisomers;
(c) reacting (III) in an aqueous organic solvent miscible mixture with a metallic reducing agent to produce a compound of the formula:

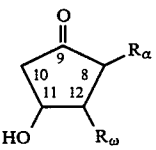 (I)

including stereoisomers as the cyclopentanoid (I).
4. A process for the preparation of a prostanoid (Ia) which comprises:
(a) reacting at reduced temperatures less than ambient temperatures of the formula:

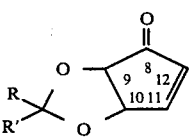

wherein R and R' together provide an acetal protecting group selected from hydrogen, lower alkyl containing 1 to 6 carbon atoms, phenyl and benzyl groups with a compound of the formula:

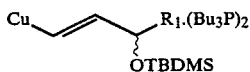

wherein $R_\omega Cu$ is a stabilized copper butyl phosphine complex of the formula:

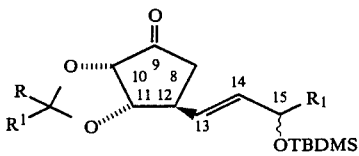

wherein $R_1$ is an alkyl group containing 1 to 8 carbon atoms and OTBDMS is a tert-butyldimethylsilyloxy group to produce an intermediate of the formula:

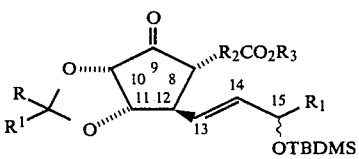

(IIa)

including stereoisomers;

(b) reacting IIa in an organic solvent with a compound of the formula: $IR_2CO_2R_3$ wherein $-R_2CO_2R_3$ is an ester group containing 2 to 6 carbon atoms and $R_3$ is a lower alkyl group containing 1 to 6 carbon atoms to produce a compound of the formula:

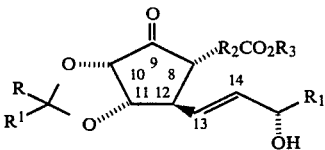

(IIIa)

including stereoisomers;

(c) reacting III with an acid or salt in an organic solvent to produce a compound of the formula:

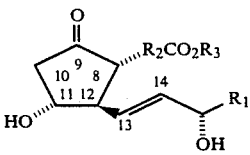

(IVa)

including stereoisomers; and (d) reacting IV with an aluminum metal mercury amalgam as a metallic reducing agent in an aqueous organic solvent mixture to produce the prostaglandin of the formula (Ia)

and including stereoisomers as the prostanoid (I).

5. A process for the preparation of a prostanoid (Ia) which comprises:

(a) reacting in an organic solvent at reduced temperatures between about $-78°$ C. and $0°$ C. a compound of the formula:

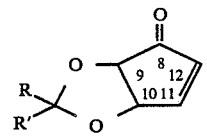

wherein R and R' are lower alkyl groups with a compound of the formula:

$R_\omega Cu$ wherein $R_\omega Cu$ is a stabilized copper butyl phosphine complex of the formula:

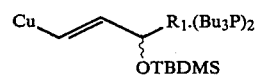

wherein $R_1$ is an alkyl group containing 1 to 8 carbon atoms and OTBDMS is a tert-butyldimethylsilyloxy group to produce an intermediate of the formula:

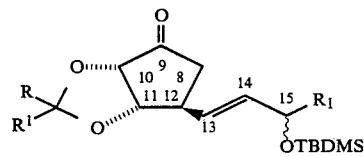

(IIa)

(b) reacting IIa in an organic solvent at a temperature between about $-30°$ C. and $0°$ C. with a compound of the formula: $IR_2CO_2R_3$ wherein $-R_2CO_2R_3$ is an alkenyl ester group and wherein $R_2$ contains 2 to 6 carbon atoms and $R_3$ is lower alkyl group containing 1 to 6 carbon atoms to produce a compound of the formula:

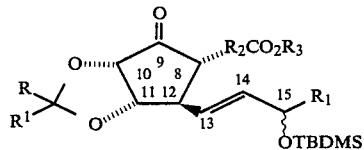

(IIIa)

(c) reacting III with an acid or salt in an organic solvent at a temperature between about $-30°$ and $0°$ C. to produce a compound of the formula:

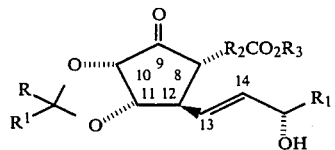

(IVa)

(d) reacting IV with an aluminum metal mercury amalgum as a metallic reducing agent in an aqueous organic solvent mixture at a temperature between about 0° and 70° C. to produce the prostaglandin of the formula:

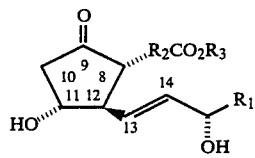

as the prostanoid (I).

6. The process of claim 4 wherein $R_1$ is pentyl and wherein $-R_2CO_2R_3$ is $-CH_2-CH=CH-(CH_2)_3-CO_2CH_3$.

7. The process of claim 4 wherein R and R' are methyl.

8. The process of claim 4 wherein $R_1$ is pentyl group.

9. The process of claim 4 wherein the organic solvent in step (a) is tetrahydrofuran wherein the organic solvent in step (b) is hexamethylphosphonictriamide, wherein in step (c) the acid is hydrofluoric acid mixed with pyridine and acetonitrile as an organic solvent and wherein the organic solvent in stepd (d) is tetrahydrofuran.

10. The process of claim 4 wherein $-R_2CO_2R_3$ is $-CH_2C\equiv C-(CH_2)_3CO_2CH_3$ and $R_1$ is pentyl.

* * * * *

UNITED STATES PATENT AND TRADEMARK OFFICE
CERTIFICATE OF CORRECTION

PATENT NO. : 4,873,360
DATED : October 10, 1989
INVENTOR(S) : Carl R. Johnson and Thomas D. Penning It is certified that error appears in the above—identified patent and that said Letters Patent is hereby corrected as shown below:

Title page under "Publications" "Roos" should be --Poos--.

Column 1, lines 57 and 58 "carboxyclic" should be --carbocyclic--.

Column 5, line 9 "to 2" should read --or 2--.

Column 5, line 46 "SYMTHESIS" should be --SYNTHESIS--.

Column 6, line 64 "Kaneki" should be --Kaneko--.

Column 7, line 45 "Kokayashi" should be --Kobayashi--.

Column 7, line 63 "mole %" should be --mol %".

Column 11, line 43 "$J_2$-3.8" should be --$J_2=3.8$--.

UNITED STATES PATENT AND TRADEMARK OFFICE
CERTIFICATE OF CORRECTION

PATENT NO. : 4,873,360
DATED : October 10, 1989
INVENTOR(S) : Carl R. Johnson and Thomas D. Penning It is certified that error appears in the above—identified patent and that said Letters Patent is hereby corrected as shown below:

Column 12, line 5 "TsOH.H$_2$O" should be --TsOH·H$_2$O--.

Column 12, line 60 "J$_2$-2.3H$_z$" should be --J$_2$=2.3H$_z$--.

Column 14, line 66 "110,61" should be --110.61--.

Column 15, line 8 "1.35 M" should be --1.34 M--.

Column 18, Scheme 40, under the first structure "($\pm$)" should be --(+)--.

Column 21, line 16 "convered" should be --converted--.

Column 21, line 68, delete "and" and insert --of-- therefor--.

Column 23, delete last chemical equation of Scheme 41 and insert therefor

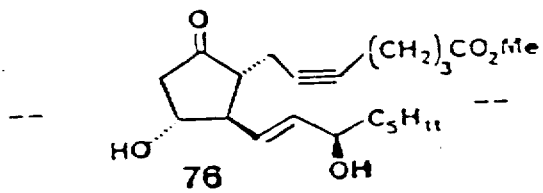

Column 25, line 8 "1.19" should be --1.91--.

Column 25, line 30 "(+)-73" should be --((+)-73--.

Column 25, lines 34 and 35 "chromatography" should be --chromatographed--.

UNITED STATES PATENT AND TRADEMARK OFFICE
CERTIFICATE OF CORRECTION

PATENT NO. : 4,873,360                              Page 3 of 3
DATED      : October 10, 1989
INVENTOR(S) : Carl R. Johnson and Thomas D. Penning It is certified that error appears in the above—identified patent and that said Letters Patent is hereby corrected as shown below:

Column 25, line 66, "11.81" should be --13.81--.

Column 26, line 1 "(-)-69)" should be --((-)-69)--.

Column 26, line 55 "(0.150 1 g" should be --(0.150 g--.

Column 30, line 51, "38.80 g" should be --33.80 g--.

Column 31, line 63 "was" should be --as--.

Column 32, line 2 "Hz, 2H9" should be --Hz, 2H)--.

Column 32, line 28 "heptynoate" should be --heptenoate--.

Column 38, line 12 "stepd" should be --step--.

Signed and Sealed this

Twenty-third Day of April, 1991

*Attest:*

HARRY F. MANBECK, JR.

*Attesting Officer*     *Commissioner of Patents and Trademarks*